US009592283B2

(12) United States Patent
Kolander et al.

(10) Patent No.: US 9,592,283 B2
(45) Date of Patent: Mar. 14, 2017

(54) **IMMUNOLOGICAL COMPOSITIONS CONTAINING ATTENUATED *HISTOPHILUS SOMNI***

(71) Applicant: MERIAL, INC., Duluth, GA (US)

(72) Inventors: Tammy Kolander, Worthington, MN (US); Paulraj Lawrence, Worthington, MN (US); Russell Bey, Arden Hills, MN (US)

(73) Assignee: MERIAL, INC., Duluth, GA (US)

( * ) Notice: Subject to any disclaimer, the term of this patent is extended or adjusted under 35 U.S.C. 154(b) by 0 days.

(21) Appl. No.: 14/668,656

(22) Filed: Mar. 25, 2015

(65) Prior Publication Data

US 2015/0273045 A1    Oct. 1, 2015

Related U.S. Application Data

(60) Provisional application No. 61/970,195, filed on Mar. 25, 2014.

(51) Int. Cl.
| | | |
|---|---|---|
| *A61K 39/102* | (2006.01) | |
| *A61K 45/06* | (2006.01) | |
| *C12N 1/36* | (2006.01) | |
| *C12N 1/38* | (2006.01) | |
| *A61K 39/00* | (2006.01) | |

(52) U.S. Cl.
CPC ............ *A61K 39/102* (2013.01); *A61K 45/06* (2013.01); *C12N 1/36* (2013.01); *C12N 1/38* (2013.01); *A61K 2039/522* (2013.01)

(58) Field of Classification Search
CPC ............ A61K 2039/522; A61K 39/102; A61K 45/06; C12N 1/36; C12N 1/38; C07K 14/47
See application file for complete search history.

(56) References Cited

U.S. PATENT DOCUMENTS 6,770,273 B1 *   8/2004   Corbeil et al. ............... 424/93.1
2011/0150933 A1 *   6/2011   Rosenbusch et al. ..... 424/264.1

OTHER PUBLICATIONS

Siddaramappa et al. BMC Genomics 12: 570, 1-20, 2011.*
Challacombe et al. 2007. Complete Genome Sequence of Haemophilus somnus (Histophilus somni) strain 129Pt and Comparison to Haemophilus ducreyi 35000 HP and Haemophilus influenzae Rd. Journal of Bacteriology 189(5); p. 1890-1898.
Geertsema, R. S. et al. 2008. Protection of mice against H. somni septicemia by vaccination with recombinant immunoglobulin binding protein subunits. Vaccine. 26:4506-4512.
Guzmán-Brambila, C et al. 2012. Two Outer Membrane Lipoproteins from H. somni are Immunogenic in Rabbits and Sheep and Induce Protection against Bacterial Challenge in Mice. Clinical and Vaccine Immunology. 19(11) : 1826-1832.
Korczak et. al. 2004. Phylogeny of the Family Pasteurellaceae based on rpoB sequences. International Journal of Systemic and Evolutionary Microbiology. 54; p. 1393-1399.
Perera, I. C. and Grove, A. 2010. Molecular Mechanisms of Ligand-Mediated Attenuation of DNA Binding by MarR Family Transcriptional Regulators. JMCB. 2(5):243-254.
Ward et al. 2006. Haemophilus somnus (Histophilus somni) in Bighorn Sheep Canadian Journal of Veterinary Research. 70; p. 34-42.

* cited by examiner

*Primary Examiner* — S. Devi
(74) *Attorney, Agent, or Firm* — Judy Jarecki-Black; Chad Kitchen; Merial Inc.

(57)    ABSTRACT

This disclosure provides attenuated *Histophilus somni* strains, compositions comprising same, and methods of production and use thereof. The attenuated strains may express lower or no levels of various virulence-associated genes, relative to the corresponding pathogenic bacteria Advantageously, the attenuated *Histophilus somni* strains may be administered orally, intranasally, intra-tracheally, or subcutaneously.

13 Claims, 1 Drawing Sheet

IMMUNOLOGICAL COMPOSITIONS CONTAINING ATTENUATED *HISTOPHILUS SOMNI*

INCORPORATION BY REFERENCE

This application claims priority to U.S. provisional application Ser. No. 61/970,195, filed on 25 Mar. 2014, and herein incorporated by reference in its entirety. All other references cited herein are also herein incorporated by reference in their entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is MER_13_225P_ST25. The text file is 17,356 KB; it was created on Feb. 20, 2014; and it is being submitted electronically via EFS-Web, concurrent with the filing of the specification.

FIELD OF THE INVENTION

The present invention relates generally to genetically engineered, attenuated bacterial vaccines, particularly those providing broad, safe, and effective protection to bovines against infections/disease caused by *Histophilus somni* (formerly *Haemophilus somnus*). The invention further relates to methods of producing the attenuated bacteria, and to the identification of nucleic acid variations that are associated with decreased pathogenicity of the attenuated bacteria.

The invention accordingly relates to immunogenic or vaccine compositions comprising the bacteria of the invention; e.g., live attenuated bacteria. The bacteria also could be inactivated in the compositions; but it may be advantageous that the bacteria are live attenuated *Histophilus somni*. The invention therefore further relates to methods for preparing and/or formulating such compositions; e.g., culturing or growing or propagating the bacteria on or in suitable medium, harvesting the bacteria, optionally inactivating the bacteria, and optionally admixing with a suitable veterinarily or pharmaceutically acceptable carrier, excipient, diluent or vehicle and/or an adjuvant and/or stabilizer. Thus, the invention also relates to the use of the bacteria in formulating such compositions.

BACKGROUND OF THE INVENTION

Bovine Respiratory Disease Complex (BRDC) consists of multiple microbial pathogens and contributes to substantial economic loss to the cattle industry. Treatment costs including both preventative vaccination and medication following an outbreak are estimated to be near $4 billion per year (Griffin, 1997). Adding to the economic impact is the associated loss in performance observed in animals diagnosed with BRDC; with measurable losses to average daily gain, body weight at harvest, and beef quality grade (Babcock, 2010). Reports on specific monetary loss associated with decreased performance vary; likely due to varying case definitions of BRDC, but are estimated between $40 (Fulton, 2002) and almost $300 (Duff and Gaylean 2011) per animal. The performance loss has also been shown to significantly increase with the number of times an animal requires treatment for BRDC (Fulton, 2002).

*Histophilus somni* (formerly *Haemophilus somnus*) has been identified as a key contributor to BRDC (Duff and Gaylean 2011). This gram-negative pleomorphic coccobacillus belonging to the family Pasterellacea (Korczak, 2004) makes up part of the normal microbiota of the upper respiratory and urogenital tracts in cattle, sheep, and other ruminants (Ward, 2006). It is closely related to other bovine pathogens including *Pasteurella multocida* and *Mannheimia haemolytica* (both of which are also associated with BRDC) as well as the human pathogens *Haemophilus ducreyi* and *Haemophilus influenzae* (Challacombe, 2007).

Estimates place the isolation rate of *H. somni* from the upper respiratory tract of healthy calves as high as 50% with no clinical manifestations of disease; however animals diagnosed with BRDC have an even higher isolation rate for the bacteria (Griffin, 2010). Under stressful conditions or states of immunosuppression, *H. somni* may colonize the lower respiratory tract, endocardium, or central nervous system and has been identified as an etiological agent in diverse diseases such as pneumonia, endocarditis, arthritis, abortion, septicemia, and thromboembolic meningoencephalitis (TEME) (Ward, 2006).

At the time of slaughter, less than 15% of animals receiving proper treatment for BRDC (preventative vaccinations and appropriate antibiotics during an outbreak) show signs of lung lesions and these lesions involve less than 5% of the total lung (Griffin, 2010). Conversely, 50% of animals not receiving proper care display lung lesions at the time of slaughter, and these lesions may involve 15% or more of the total lung (Griffin, 2010). In one field study of over 10,000 animals, 459 calves (4.6%) died from disease of one form or another. Of the mortalities in the study, 279 (60.8%) were shown to be related to respiratory ailments, and of those with respiratory infections, 226 (81.0%) were associated with *H. somni* related pneumonia, pleurisy, or abscesses (Ribble, 1988). While antibiotic treatment may be successful in response to an *H. somni* infection, an increasing prevalence of antibiotic resistant field isolates is of concern (Duff and Gaylean, 2011). Preventative care by vaccination would be preferred as it is proactive rather than reactive and is much more cost effective.

Many *H. somni* vaccines are currently available from various animal health companies; however these vaccines are predominantly composed of killed bacterins and were licensed over thirty years ago with an aim in preventing TEME. The use of these bacterin vaccines has been effective against TEME, however has been shown to have neutral or even negative effects on respiratory disease in feedlot cattle. Negative side-effects include IgE induced anaphylactic shock and interactions when calves infected with Bovine Respiratory Syncytial Virus (BRSV) are vaccinated (Griffin, 2010). The decrease in prevalence of TEME and the emergence of *H. somni* related pneumonia in the US and myocarditis in Canada beginning in the late 1980's, have led to a need for further investigation of efficacious antigens for vaccine production (O'Toole, 2009).

*H. somni* related pneumonia is an economically significant condition for the beef and dairy industries. There is little evidence of field efficacy in currently available vaccines, so the need for research into next generation vaccine products is warranted.

SUMMARY OF THE INVENTION

An object of this invention is to provide attenuated bacteria as well as methods for treatment and prophylaxis of infection by *H. somni*.

In an embodiment, the vaccines comprise attenuated *H. somni*, which are less pathogenic as compared to a more virulent strain. Comprehensive comparative sequence analysis revealed the absence of important virulence factors in the attenuated *H. somni* strains, relative to more virulent strains. Thus, it is an object of the invention to provide attenuated *H. somni*, which are lacking in virulence factors possessed by more virulent *H. somni* strains.

As defined herein, the term "gene" will be used in a broad sense, and shall encompass both coding and non-coding sequences (i.e. upstream and downstream regulatory sequences, promoters, 5'/3' UTR, introns, and exons). Where reference to only a gene's coding sequence is intended, the term "gene's coding sequence" or "CDS" will be used interchangeably throughout this disclosure. When a specific nucleic acid is discussed, the skilled person will instantly be in possession of all derivable forms of that sequence (mRNA, vRNA, cRNA, DNA, protein, etc.).

The invention further provides methods for inducing an immunological (or immunogenic) or protective response against *H. somni*, as well as methods for preventing or treating *H. somni*, or disease state(s) caused by *H. somni*, comprising administering the attenuated *H. somni*, or a composition comprising the attenuated *H. somni* to animals in need thereof. Moreover, kits comprising at least the attenuated *H. somni* strain(s) and instructions for use are also provided.

These and other embodiments are disclosed or are obvious from and encompassed by, the following Detailed Description.

BRIEF DESCRIPTION OF DRAWINGS

A full and enabling disclosure of the present invention, including the best mode thereof, to one of ordinary skill in the art, is set forth more particularly in the remainder of the specification, including reference to the accompanying figures, wherein.

DETAILED DESCRIPTION OF THE INVENTION

Figure 1:
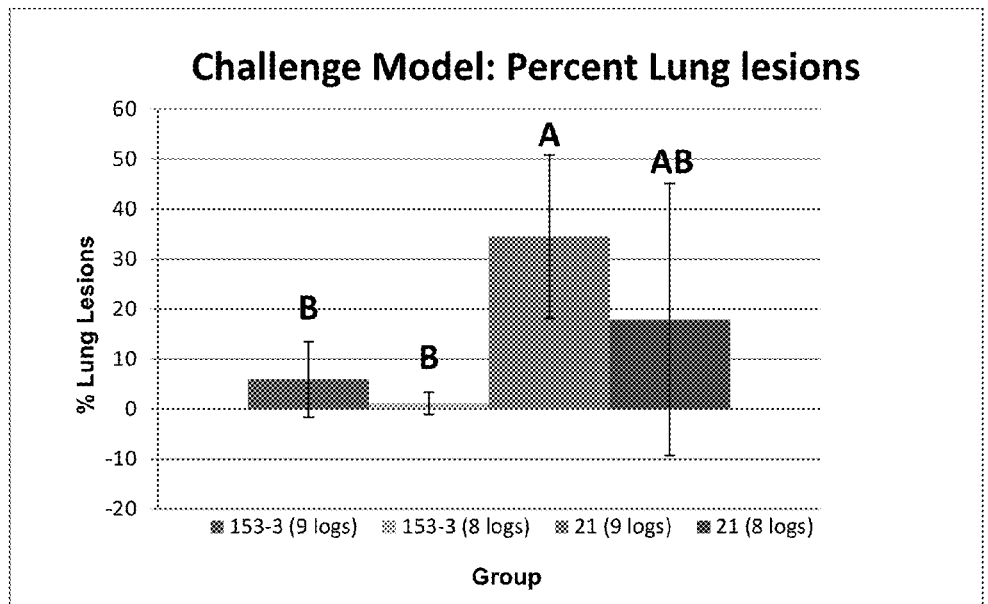
FIG. 1 shows the average percent lung lesions for each isolate and dose tested in the challenge model. Groups with different letters are significantly different according to Student's t performed on the arcsine transformed data.

The present invention provides nucleotide sequences and genes involved in the attenuation of a microorganism, such as bacteria, for instance, *H. somni*, products (e.g., proteins, antigens, immunogens, epitopes) encoded by the nucleotide sequences, methods for producing such nucleotide sequences, products, micro-organisms, and uses thereof, such as for preparing vaccine or immunogenic compositions or for eliciting an immunological or immune response or as a vector, e.g., as an expression vector (for instance, an in vitro or in vivo expression vector).

Mutations identified in nucleotide sequences and genes of micro-organisms produce novel and nonobvious attenuated mutants. These mutants are useful for the production of live attenuated immunogenic compositions or live attenuated vaccines having a high degree of immunogenicity.

Identification of the mutations provides novel and non-obvious nucleotide sequences and genes, as well as novel and nonobvious gene products encoded by the nucleotide sequences and genes.

In an embodiment, the invention provides an attenuated *H. somni* strain capable of providing a safe and effective immune response in cattle against *H. somni* or diseases caused by *H. somni*.

In an aspect, the invention provides bacteria containing an attenuating mutation in a nucleotide sequence or a gene wherein the mutation modifies the biological activity of a polypeptide or protein encoded by a gene, resulting in attenuated virulence of the bacteria.

In particular, the present invention encompasses attenuated *H. somni* strains and vaccines comprising the same, which elicit an immunogenic response in an animal, particularly the attenuated *H. somni* strains that elicit, induce or stimulate a response in a bovine.

Particular *H. somni* attenuated strains of interest have mutations in genes, relative to virulent strains. It is recognized that, in addition to strains having the disclosed mutations, attenuated strains having any number of mutations in the disclosed virulence genes can be used in the practice of this invention.

In another aspect, the novel attenuated *H. somni* strains are formulated into safe, effective vaccine against *H. somni* and infections/diseases cause by *H. somni*.

In an embodiment, the attenuated *H. somni* strain is capable of providing a safe and effective immune response in a bovine against *H. somni* or diseases caused by *H. somni*.

In a particular embodiment, the attenuated strain is lacking one or several virulence genes, relative to an otherwise genetically similar virulent strain. In an embodiment, the attenuated strain lacks and/or does not express the glycoside hydrolase family protein (HSM_1160) and the lipoprotein (HSM_1714). Absent genes that may also be contribute to the strain's attenuated phenotype include: multicopper oxidase type 3 (HSM_1726) and a TetR family transcriptional regulator (HSM_1734). In an even more particular embodiment, the attenuated strain is the same as that deposited in the ATCC under the designation PTA-121029.

In an embodiment, the strain may be administered intra-nasally or subcutaneously.

In another aspect, the invention encompasses an immunological composition comprising the disclosed attenuated *H. somni* strains. The composition may further comprise a pharmaceutically or veterinary acceptable vehicle, diluent or excipient.

In an embodiment, the composition may provide a safe and protective immune response in bovine against subsequent virulent *H. somni* challenge.

In still another embodiment, the composition may comprise a genetically engineered, non-naturally-occurring, attenuated *H. somni* strain, suitable for use in a safe and effective vaccine formulation, and having at least the following genes mutated, including completely deleted, to eliminate the ability of the genes to express their cognate gene product: HSM_0270, HSM_0338, HSM_0377, HSM_0598, HSM_0708, HSM_0749, HSM_0953, HSM_1160, HSM_1191, HSM_1257, HSM_1426, HSM_1616, HSM_1624, HSM_1728, HSM_1730, HSM_1734, HSM_1736, HSM_1737, HSM_1741, HSM_1793 and HSM_1889. In a particular embodiment, the engineered *H. somni* strain has an identical attenuated phenotype as compared with TK #4.

In a related embodiment, the composition may comprise a genetically engineered, non-naturally-occurring, attenuated *H. somni* strain, suitable for use in a safe and effective vaccine formulation, and having a sufficient number of the following genes mutated, including completely deleted, to eliminate the ability of the genes to express their cognate gene product: HSM_0270, HSM_0338, HSM_0377, HSM_0598, HSM_0708, HSM_0749, HSM_0953, HSM_1160, HSM_1191, HSM_1257, HSM_1426, HSM_1616, HSM_1624, HSM_1728, HSM_1730, HSM_1734, HSM_1736, HSM_1737, HSM_1741, HSM_1793 and HSM_1889. In a particular embodiment, the engineered *H. somni* strain has an identical attenuated phenotype as compared with TK #4.

In another embodiment, the composition may comprise a genetically engineered, non-naturally-occurring, attenuated *H. somni* strain, suitable for use in a safe and effective vaccine formulation, and having at least the following genes mutated, including completely deleted, to eliminate the ability of the gene to express its cognate gene product: HSM_0077, HSM_0270, HSM_0708, HSM_0975, HSM_1191, HSM_1257, HSM_1448, HSM_1542, HSM_1571, HSM_1624, HSM_1714, HSM_1726, HSM_1728, HSM_1730, HSM_1734, HSM_1736, HSM_1737, HSM_1741 and HSM_1793. In a particular embodiment, the engineered *H. somni* strain has an identical attenuated phenotype as compared with TK #42.

In a related embodiment, the composition may comprise a genetically engineered, non-naturally-occurring, attenuated *H. somni* strain, suitable for use in a safe and effective vaccine formulation, and having a sufficient number of the following genes mutated, including completely deleted, to eliminate the ability of the gene to express its cognate gene product: HSM_0077, HSM_0270, HSM_0708, HSM_0975, HSM_1191, HSM_1257, HSM_1448, HSM_1542, HSM_1571, HSM_1624, HSM_1714, HSM_1726, HSM_1728, HSM_1730, HSM_1734, HSM_1736, HSM_1737, HSM_1741 and HSM_1793. In a particular embodiment, the engineered *H. somni* strain has an identical attenuated phenotype as compared with TK #42.

In another embodiment, the composition may comprise a genetically engineered, non-naturally-occurring, attenuated *H. somni* strain, suitable for use in a safe and effective vaccine formulation, and having at least the following genes mutated, including completely deleted, to eliminate the ability of the gene to express its cognate gene product: HSM_0268, HSM_0270, HSM_0274, HSM_0598, HSM_0708, HSM_0749, HSM_0938, HSM_1022, HSM_1160, HSM_1191, HSM_1212, HSM_1257, HSM_1542, HSM_1571, HSM_1667, HSM_1728, HSM_1730, HSM_1736, HSM_1737, HSM_1741, HSM_1793 and HSM_1889. In a particular embodiment, the engineered *H. somni* strain has an identical attenuated phenotype as compared with TK #34.

In a related embodiment, the composition may comprise a genetically engineered, non-naturally-occurring, attenuated *H. somni* strain, suitable for use in a safe and effective vaccine formulation, and having a sufficient number of the following genes mutated, including completely deleted, to eliminate the ability of the gene to express its cognate gene product: HSM_0268, HSM_0270, HSM_0274, HSM_0598, HSM_0708, HSM_0749, HSM_0938, HSM_1022, HSM_1160, HSM_1191, HSM_1212, HSM_1257, HSM_1542, HSM_1571, HSM_1667, HSM_1728, HSM_1730, HSM_1736, HSM_1737, HSM_1741, HSM_1793 and HSM_1889. In a particular embodiment, the engineered *H. somni* strain has an identical attenuated phenotype as compared with TK #34.

Now that Applicants have disclosed these sufficient sets of attenuating gene deletions, the skilled person will appreciate that only non-routine works remains to determine which sub-combinations of these gene deletions are necessary to produce comparably- or equivalently-attenuated *H. somni* vaccine strains.

In another embodiment, the composition may further comprise at least one additional antigen associated with or derived from a bovine pathogen other than *H. somni*.

In an embodiment, the at least one or more additional antigen(s) is capable of eliciting in a cattle an immune response against *H. somni*, bovine respiratory disease complex (BRDC), bovine respiratory syncytial virus (BRSV), bovine viral diarrhea (BVD), bovine parainfluenza 3 (PI3), infectious bovine rhinotracheitis (IBR), bovine herpesvirus-1 (BHV-1), bluetongue disease virus (BTV), or any other pathogen capable of infecting and causing illness or susceptibility to illness in a bovine.

In another aspect, the invention provides a method of vaccinating an animal comprising administration of at least one of the disclosed immunological compositions comprising the attenuated *H. somni* strains.

In an embodiment, the *H. somni* vaccines further comprise an adjuvant. In a particular embodiment, the adjuvant comprises whole bacteria and/or bacteria, including *clostridium, H. somni, Mannheimia, Pasteurella, Histophilus, Salmonella, Escherichia coli*, or combinations and/or variations thereof. In several embodiments, the adjuvant increases the animal's production of IgM, IgG, IgA, and/or combinations thereof.

In another embodiment, the invention provides an attenuated *Histophilus somni* (*H. somni*) strain, which is capable of providing a safe and effective immune response in a bovine animal against *H. somni*, or diseases caused by *H. somni*; wherein the attenuated strain lacks, in its genomic sequence, a minimum number of virulence factor-encoding genes, relative to a reference virulent *H. somni* strain, to render the attenuated strain incapable of causing infection in the bovine animal.

In an embodiment, the reference virulent strain comprises a genomic DNA sequence, which encodes at least about 99% of the same genes as does the sequence as set forth in SEQ ID NO:2. In other embodiments, the attenuated strain encodes at least about 99% of the same genes as does the sequence as set forth in SEQ ID NO:1, 3, 4, or 5. In a particular embodiment, the attenuated strain(s) expresses any virulence factor gene at a level about equal to, or lower than (including an undetectable level), the level of the corresponding virulence gene expressed by an attenuated strain having for its genome the sequence as set forth in SEQ ID NO:1, 3, 4, or 5.

In a particular embodiment, the attenuated strain lacks at least about 99% of the same genes, relative to *H. somni* strain 2336, as does *H. somni* strain #4. In this embodiment, strain 2336 comprises a genomic sequence, which encodes at least about 99% of the same genes as does the sequence as set forth in SEQ ID NO:6; and strain #4 comprises a genomic sequence, which encodes at least about 99% of the same genes as does the sequence as set forth in SEQ ID NO:1.

In a particular embodiment, the attenuated strain is the #4 isolate (i.e. TK #4), which is deposited at the ATCC under the designation PTA-121029. In another embodiment, the attenuated strain is the #42 isolate (i.e. TK #42), which is deposited at the ATCC under the designation PTA-121030.

In another aspect, the invention provides immunological compositions comprising any of the attenuated strains described herein. In an embodiment, the composition comprises an attenuated strain, which encodes at least about 99% of the same genes as does the sequence as set forth in SEQ ID NO:1, 3, 4 or 5.

In one particular embodiment, the attenuated strain encodes at least about 99% of the same genes as does the sequence as set forth in SEQ ID NO:1. In a related embodiment, the attenuated strain encodes all the same genes as does the sequence as set forth in SEQ ID NO:1.

In one embodiment, the attenuated strain encodes at least about 99% of the same genes as does the sequence as set forth in SEQ ID NO:4. In a related embodiment, the attenuated strain encodes all the same genes as does the sequence as set forth in SEQ ID NO:4.

In still another embodiment, the attenuated strain encodes at least about 99% of the same genes as does the sequence as set forth in SEQ ID NO:3. In a related embodiment, the attenuated strain encodes all the same genes as does the sequence as set forth in SEQ ID NO:3.

In yet another embodiment, the attenuated strain encodes at least about 99% of the same genes as does the sequence as set forth in SEQ ID NO:5. In related embodiment, the attenuated strain encodes all the same genes as does the sequence as set forth in SEQ ID NO:5.

In an embodiment, the immunological composition further comprises a pharmaceutically or veterinary acceptable vehicle, diluent or excipient.

In a particular embodiment, immunological composition is capable of eliciting in a bovine animal a protective immune response, which protects the bovine against a subsequent exposure to a virulent *H. somni* strain.

In another embodiment, the immunological composition further comprises at least one or more additional antigen, which is capable of eliciting in a bovine animal a pathogen-specific immune response. In a particular embodiment, the at least one or more additional antigen elicits in the bovine an immune response sufficient to protect the animal from a subsequent exposure to the pathogen from which the antigen was derived. Thus, if a bovine PI3 antigen is included as a component of the immunological composition, the composition should elicit a protective immune response.

In another embodiment, the additional antigen is capable of eliciting in a bovine animal an immune response, which will enhance the animal's immune response against a subsequent exposure to Bovine Respiratory Disease Complex, BRSV, BVD, PI3 or any other pathogen capable of infecting and causing illness or susceptibility to illness in a bovine animal. For example, a BRSV antigen will provide protection against a subsequent exposure to virulent BRSV.

In another aspect, the invention provides a method of vaccinating a bovine animal comprising the step of administering to the bovine animal at least one dose of an immunological composition as herein described.

By "antigen" or "immunogen" means a substance that induces a specific immune response in a host animal. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a polypeptide, an epitope, a hapten, or any combination thereof. Alternately, the immunogen or antigen may comprise a toxin or antitoxin.

The terms "protein", "peptide", "polypeptide" and "polypeptide fragment" are used interchangeably herein to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

The term "immunogenic or antigenic polypeptide" as used herein includes polypeptides that are immunologically active in the sense that once administered to the host, it is able to evoke an immune response of the humoral and/or cellular type directed against the protein. Preferably the protein fragment is such that it has substantially the same immunological activity as the total protein. Thus, a protein fragment according to the invention comprises or consists essentially of or consists of at least one epitope or antigenic determinant. An "immunogenic" protein or polypeptide, as used herein, includes the full-length sequence of the protein, analogs thereof, or immunogenic fragments thereof. By "immunogenic fragment" is meant a fragment of a protein which includes one or more epitopes and thus elicits the immunological response described above. Such fragments can be identified using any number of epitope mapping techniques, well known in the art. See, e.g., Epitope Mapping Protocols in Methods in Molecular Biology, Vol. 66 (Glenn E. Morris, Ed., 1996). For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al., 1984; Geysen et al., 1986. Similarly, conformational epitopes are readily identified by determining spatial conformation of amino acids such as by, e.g., x-ray crystallography and 2-dimensional nuclear magnetic resonance. See, e.g., Epitope Mapping Protocols, supra. Methods especially applicable to the proteins of *T. parva* are fully described in PCT/US2004/022605 incorporated herein by reference in its entirety.

As discussed herein, the invention encompasses active fragments and variants of the antigenic polypeptide. Thus, the term "immunogenic or antigenic polypeptide" further contemplates deletions, additions and substitutions to the sequence, so long as the polypeptide functions to produce an immunological response as defined herein. The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cystine, serine, threonine, tyrosine. Phenylalanine, tryptophan, and tyrosine are sometimes classified as aromatic amino acids. Examples of conservative variations include the substitution of one hydrophobic residue such as isoleucine, valine, leucine or methionine for another hydrophobic residue, or the substitution of one polar residue for another polar residue, such as the substitution of arginine for lysine, glutamic acid for aspartic acid, or glutamine for asparagine, and the like; or a similar conservative replacement of an amino acid with a structurally related amino acid that will not have a major effect on the biological activity. Proteins having substantially the same amino acid sequence as the reference molecule but possessing minor amino acid substitutions that do not substantially affect the immunogenicity of the protein are, therefore, within the definition of the reference polypeptide. All of the polypeptides produced by these modifications are included herein. The term "conservative variation" also includes the use of a substituted amino acid in place of an unsubstituted parent amino acid provided that antibodies raised to the substituted polypeptide also immunoreact with the unsubstituted polypeptide.

The term "epitope" refers to the site on an antigen or hapten to which specific B cells and/or T cells respond. The term is also used interchangeably with "antigenic determinant" or "antigenic determinant site". Antibodies that recognize the same epitope can be identified in a simple immunoassay showing the ability of one antibody to block the binding of another antibody to a target antigen.

An "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms and/or clinical disease signs normally displayed by an infected host, a quicker recovery time and/or a lowered viral titer in the infected host.

By "animal" is intended mammals, birds, and the like. Animal or host as used herein includes mammals and human. The animal may be selected from the group consisting of equine (e.g., horse), canine (e.g., dogs, wolves, foxes, coyotes, jackals), feline (e.g., lions, tigers, domestic cats, wild cats, other big cats, and other felines including cheetahs and lynx), ovine (e.g., sheep), bovine (e.g., cattle, calves, steers, bulls), porcine (e.g., pig), avian (e.g., chicken, duck, goose, turkey, quail, pheasant, parrot, finches, hawk, crow, ostrich, emu and cassowary), primate (e.g., prosimian, tarsier, monkey, gibbon, ape), ferrets, seals, and fish. The term "animal" also includes an individual animal in all stages of development, including newborn, embryonic and fetal stages.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Similarly, the word "or" is intended to include "and" unless the context clearly indicate otherwise.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

Compositions

The present invention relates to a H. somni vaccine or composition which may comprise an attenuated H. somni strain and a pharmaceutically or veterinarily acceptable carrier, excipient, or vehicle, which elicits, induces or stimulates a response in an animal.

The term "nucleic acid" and "polynucleotide" refers to RNA or DNA that is linear or branched, single or double stranded, or a hybrid thereof. The term also encompasses RNA/DNA hybrids. The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracyl, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support. The polynucleotides can be obtained by chemical synthesis or derived from a microorganism.

The term "gene" is used broadly to refer to any segment of polynucleotide associated with a biological function. Thus, genes include introns and exons as in genomic sequence, or just the coding sequences as in cDNAs and/or the regulatory sequences required for their expression. For example, gene also refers to a nucleic acid fragment that expresses mRNA or functional RNA, or encodes a specific protein, and which includes regulatory sequences.

An "isolated" biological component (such as a nucleic acid or protein or organelle) refers to a component that has been substantially separated or purified away from other biological components in the cell of the organism in which the component naturally occurs, for instance, other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant technology as well as chemical synthesis.

The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, as described above.

The term "recombinant" means a polynucleotide with semisynthetic, or synthetic origin which either does not occur in nature or is linked to another polynucleotide in an arrangement not found in nature.

"Heterologous" means derived from a genetically distinct entity from the rest of the entity to which it is being compared. For example, a polynucleotide may be placed by genetic engineering techniques into a plasmid or vector derived from a different source, and is a heterologous polynucleotide. A promoter removed from its native coding sequence and operatively linked to a coding sequence other than the native sequence is a heterologous promoter.

The polynucleotides of the invention may comprise additional sequences, such as additional encoding sequences within the same transcription unit, controlling elements such as promoters, ribosome binding sites, 5'UTR, 3'UTR, transcription terminators, polyadenylation sites, additional transcription units under control of the same or a different promoter, sequences that permit cloning, expression, homologous recombination, and transformation of a host cell, and any such construct as may be desirable to provide embodiments of this invention.

Methods of use and Article of Manufacture

The present invention includes the following method embodiments. In an embodiment, a method of vaccinating an animal comprising administering a composition comprising an attenuated *H. somni* strain and a pharmaceutical or veterinarily acceptable carrier, excipient, or vehicle to an animal is disclosed. In one aspect of this embodiment, the animal is a bovine.

In one embodiment of the invention, a prime-boost regimen can be employed, which is comprised of at least one primary administration and at least one booster administration using at least one common polypeptide, antigen, epitope or immunogen. Typically the immunological composition or vaccine used in primary administration is different in nature from those used as a booster. However, it is noted that the same composition can be used as the primary administration and the booster administration. This administration protocol is called "prime-boost".

A prime-boost regimen comprises at least one prime-administration and at least one boost administration using at least one common polypeptide and/or variants or fragments thereof. The vaccine used in prime-administration may be different in nature from those used as a later booster vaccine. The prime-administration may comprise one or more administrations. Similarly, the boost administration may comprise one or more administrations.

The dose volume of compositions for target species that are mammals, e.g., the dose volume of cattle or bovine compositions, based on bacterial antigens, is generally between about 0.1 to about 2.0 ml, between about 0.1 to about 1.0 ml, and between about 0.5 ml to about 1.0 ml.

The efficacy of the vaccines may be tested about 3 to 5 weeks after the last immunization by challenging animals, such as bovine, with a virulent, heterologous strain of *H. somni*. The animal may be challenged intra-nasally, intra-tracheally, and/or trans-tracheally. Samples from nasal passages, trachea, lungs, brain, and/or mouth may be collected before and post-challenge and may be analyzed for the presence of *H. somni*-specific antibody.

The compositions comprising the attenuated viral strains of the invention used in the prime-boost protocols are contained in a pharmaceutically or veterinary acceptable vehicle, diluent or excipient. The protocols of the invention protect the animal from *H. somni* and/or prevent disease progression in an infected animal.

The various administration is preferably a one-shot dosage, but multiple dosages could be carried out 1 to 6 weeks apart. A preferred time interval is 2 to 3 weeks, and an annual booster is also envisioned. In an embodiment, the compositions are administered to calves that are between about 5 to about 6 weeks old. In another embodiment, the calves may be about 3 to about 4 weeks old.

It should be understood by one of skill in the art that the disclosure herein is provided by way of example and the present invention is not limited thereto. From the disclosure herein and the knowledge in the art, the skilled artisan can determine the number of administrations, the administration route, and the doses to be used for each injection protocol, without any undue experimentation.

Another embodiment of the invention is a kit for performing a method of eliciting or inducing an immunological or protective response against *H. somni* in an animal comprising an attenuated *H. somni* immunological composition or vaccine and instructions for performing the method of delivery in an effective amount for eliciting an immune response in the animal.

Another embodiment of the invention is a kit for performing a method of inducing an immunological or protective response against *H. somni* in an animal comprising a composition or vaccine comprising an attenuated *H. somni* strain of the invention, and instructions for performing the method of delivery in an effective amount for eliciting an immune response in the animal.

The pharmaceutically or veterinarily acceptable carriers or vehicles or excipients are well known to one skilled in the art. For example, a pharmaceutically or veterinarily acceptable carrier or vehicle or excipient can be a 0.9% NaCl (e.g., saline) solution or a phosphate buffer. Other pharmaceutically or veterinarily acceptable carrier or vehicle or excipients that can be used for methods of this invention include, but are not limited to, poly-(L-glutamate) or polyvinylpyrrolidone. The pharmaceutically or veterinarily acceptable carrier or vehicle or excipients may be any compound or combination of compounds facilitating the administration of the attenuated bacteria. Doses and dose volumes are herein discussed in the general description and can also be determined by the skilled artisan from this disclosure read in conjunction with the knowledge in the art, without any undue experimentation.

Though the disclosed results were obtained without the use of an adjuvant, the immunological compositions and vaccines may further comprise or consist essentially of an appropriate adjuvant. Suitable adjuvants for use in the practice of the present invention are (1) polymers of acrylic or methacrylic acid, maleic anhydride and alkenyl derivative polymers, (2) immunostimulating sequences (ISS), such as oligodeoxyribonucleotide sequences having one or more non-methylated CpG units (Klinman et al., 1996; WO98/16247), (3) an oil in water emulsion, such as the SPT emulsion described on page 147 of "Vaccine Design, The Subunit and Adjuvant Approach" published by M. Powell, M. Newman, Plenum Press 1995, and the emulsion MF59 described on page 183 of the same work, (4) cationic lipids containing a quaternary ammonium salt, e.g., DDA (5) cytokines, (6) aluminum hydroxide or aluminum phosphate, (7) saponin or (8) other adjuvants discussed in any document cited and incorporated by reference into the instant application, or (9) any combinations or mixtures thereof.

In an embodiment, adjuvants include those which promote improved absorption through mucosal linings. Some examples include MPL, LTK63, toxins, PLG microparticles and several others (Vajdy, M. Immunology and Cell Biology (2004) 82, 617-627). In an embodiment, the adjuvant may be a chitosan (Van der Lubben et al. 2001; Patel et al. 2005; Majithiya et al. 2008; U.S. Pat. No. 5,980,912).

REFERENCES

Alekshun, M. N. and Levy, S. B. 2007. Molecular mechanisms of antibacterial multidrug resistance. *Cell*. 128(6): 1037-1050.

Asgarali, A. Stubbs, K. A., Oliver, A., Vocaldo, D. J., and Mark, B. L. 2009. Inactivation of the Glycoside Hydrolase NagZ Attenuates Antipseudomonal β-Lactam Resistance in *Pseudomonas aeruginosa*. *Antimicrobial Agents and Chemotherapy.* 53(6):2274-2282.

Aubry, C et al. 2011. OatA, a peptidoglycan O-acetyltransferase involved in *Listeria monocytogenes* immune escape, is critical for virulence. *J. Infect. Dis.* 204(5):731-740.

Babcock, A. H. 2010. Epidemiology of Bovine Respiratory Disease and Mortality in Commercial Feedlots. Kansas State University (doctoral dissertation).

Berghaus, L. J., Corbeil, L. B., Berghaus, R. D., Kalina, W. V., Kimball, R. A., and Gershwin, L. J. 2006. Effects of dual vaccination for bovine respiratory syncytial virus and *Haemophilus somnus* on immune responses. Vaccine. 24:6018-6027.

Brown, N. L., Stoyanov, J. V., Kidd, S. P., and Hobman J. L. 2003. The MerR family of transcriptional regulators. *FEMS Microbiology Reviews.* 27:145-163.

Challacombe et al. 2007. Complete Genome Sequence of *Haemophilus somnus* (*Histophilus somni*) strain 129Pt and Comparison to *Haemophilus ducreyi* 35000HP and *Haemophilus influenzae* Rd. Journal of Bacteriology 189 (5); p 1890-1898.

Corbeil, L. B. et. al. 1985. Serum susceptibility of *Haemophilus somnus* from bovine clinical cases and carriers. *Journal of Clinical Microbiology.* 22(2):192-198.

Cox, A. D., Howard, M. D., Brisson, J.-R., Van Der Zwan M., Thibault, P., Perry, M. B., and Inzana, T. J. 1998. Structural analysis of the phase-variable lipooligosaccharide from *Haemophilus somnus* strain 738. European Journal of Biochemistry. 97:253(2):507-516.

Daines D. A., Jarisch J., and Smith A. L. 2004. Identification and characterization of a nontypeable *Haemophilus influenzae* putative toxin-antitoxin locus. *BMC Microbiol.* July 26; 4:30.

Duff and Gaylean 2011. Recent Advances in Management of Highly Stressed, Newly Received Feedlot Cattle. *Journal of Animal Science.* 85; p 823-840.

Garbe, J. and Collin, M. 2012. Bacterial Hydrolysis of Host Glycoproteins—Powerful Protein Modification and Efficient Nutrient Acquisition. *Journal of Innate Immunity.* 4:121-131.

Fulton, R. W. et al. 2002. Evaluation of Health Status of Calves and the Impact on Feedlot Performances: Assessment of a Retained Ownership Program for Postweaning Calves. *Can. J. Vet. Res.* 66, 173-180.

Geertsema, R. S., Worby, C., Kruger, R. P., Tagawa, Y., Russo, R., Herdman, D. S., Lo, K. Kimball, R. A., Dixon, J., and Corbeil, L. B. 2008. Protection of mice against *H. somni* septicemia by vaccination with recombinant immunoglobulin binding protein subunits. Vaccine. 26:4506-4512.

Gershwin, L. J., Berghaus, L. J. Arnold, K., Anderson, M. L., and Corbeil, L. B. 2005. Immune mechanisms of pathogenic synergy in concurrent bovine pulmonary infection with *Haemophilus somnus* and bovine respiratory syncytial virus. 2005. Veterinary Immunology and Immunopathology. 107:119-130.

Griffin, D. 2010, Bovine Pasteurellosis and other Bacterial Infections of the Respiratory Tract. *Vet. Clin. North Am. Food Anim. Pract.* 26(1); p57-71.

Griffin, D. 1997. Economic Impact Associated with Respiratory Disease in Beef Cattle. *Vet. Clin. North Am. Food Anim. Pract.* 13; p367-377.

Guzmán-Brambila, C et al. 2012. Two Outer Membrane Lipoproteins from *H. somni* are Immunogenic in Rabbits and Sheep and Induce Protection against Bacterial Challenge in Mice. *Clinical and Vaccine Immunology.* 19(11): 1826-1832.

Huston, W. M., Jennings, M. P., McEwan, A. G. 2002. The multicopper oxidase of *Pseudomonas aeruginosa* is a ferroxidase with a central role in iron acquisition. *Molecular Microbiology.* 45(6):1741-1750.

Kahler, C. et. al. 1996. IgtF and RfaK constitute the lipooligosaccharide ice (inner core extension) biosynthesis operon of *N. meningitidis*. *J. Bacteriology.* December 6677-6684.

Kjos, M., Snipen, L., Salehian, Z., Nes, I. F., and Diep, D. B. 2010. The Abi proteins and their involvement in bacteriocin self-immunity. *Journal of Bacteriology.* 192 (8):2068-2076.

Korczak et. al. 2004. Phylogeny of the Family Pasteurellaceae based on rpoB sequences. International Journal of Systemic and Evolutionary Microbiology. 54; p 1393-1399.

Liu, T. et. al. 2008. Immunological responses against *S. enterica* serovar *Typhimurium* Braun lipoprotein and lipid A mutant strains in Swiss-Webster mice: Potential use as live-attenuated vaccines. *Microbial Pathogenesis.* 44(3): 224-237.

Perera, I. C. and Grove, A. 2010. Molecular Mechanisms of Ligand-Mediated Attenuation of DNA Binding by MarR Family Transcriptional Regulators. *JMCB.* 2(5):243-254.

O'Toole et al. 2009. Diagnostic Exercise: Myocarditis due to *Histophilus somni* in Feedlot and Backgrounded Cattle. *Veterinary Pathology.* 46; p 1015-1017.

Ramos, J. L., Martinez-Bueno, M., Molina-Henares, A. J., Terin, W., Watanabe, K., Zhang, X., Trinidad Gallegos, M., Brennan, R., and Tobes, R. 2005. The TetR family of Transcriptional Repressors. *MMBR.* 69:326-356.

Ribble et al. 1988. Efficacy of Immunization of Feedlot Cattle with a Commercial *Haemophilus* somnus bacterin. *Canadian Journal of Veterinary Research.* 52; p 191-198.

Schäfer, A et al. 1994. Cloning and characterization of a DNA region encoding a stress-sensitive restriction system from *Corynebacterium glutamicum* ATCC 13032 and analysis of its role in intergenic conjugation with *E. coli*. *J. Bacteriology.* 176(23):7309-7319.

Ward et al. 2006. *Haemophilus somnus* (*Histophilus somni*) in Bighorn Sheep. *Canadian Journal of Veterinary Research.* 70; p. 34-42.

The invention will now be further described by the following non-limiting examples.

EXAMPLES

The literature has reported on a number of *H. somni* virulence factors. No single virulence factor seems to dominate the role of the pathogen, but instead, several factors appear to act in concert to make a given isolate virulent. Seven virulence factors were identified: DR2 (a direct repeat that contains a conserved cytotoxic Fic motif within the IbpA domain involved in resistance to serum), hsst-I (CMP-Neu5Ac-β-Gal-α-(2-3)-sialyltransferase, where sialylation of the lipooligosaccharide (LOS) has been shown to inhibit antibody binding), lob2b (encoding a glycotransferase involved in LOS synthesis), nan lyase (N-acetylneuraminate lyase, involved in sialic acid metabolism), nan epimerase (N-acetylmannosamine-6-phosphate-2-epimerase, involved in the transport and metabolism of carbohydrates), luxS (involved in AI-2 quorum sensing), and uspE (a universal stress protein necessary for cell motility and aggregation in biofilm formation). Primers were designed to amplify each of these genes and PCR reaction parameters were optimized.

Fifty isolates were selected for screening. The criteria for isolate selection was they had to be isolated within approximately one year of the start of this study and had to be from diverse geographical locations or from cases of particular interest with high possible genotypic diversity. The purpose of this was to look at the most current isolates indicative of *H. somni* in the field and also to try and screen as much diversity as possible. Isolates were evaluated on their growth and colony appearance, in addition to carrying out the PCR reactions defined for each virulence factor of interest. The PCR reactions were visualized on a 1% agarose gel. Following the selection of isolates based on growth, colony appearance, and PCR results, animal models were identified and used to evaluate isolates of interest.

Example 1

*H. somni* Mouse Challenge Model Development

Based on growth, geographical diversity, and sequence information, 21 isolates were selected for evaluation in mice (Table 1).

TABLE 1

Isolates evaluated for a naturally occurring *H. somni* vaccine candidate.

| Isolate # | Case # | Location | SEQ ID NO |
|---|---|---|---|
| TK #1 | 12-0137-7 | Grandview, ID | |
| TK #2 | 12-0137-8 | Grandview, ID | |
| TK #3 | 12-0137-9 | Grandview, ID | |
| TK #4 | 12-0137-4 | Grandview, ID | 1 |
| TK #5 | 12-0137-6 | Grandview, ID | |
| TK #14 | 12-0137-13 | Grandview, ID | |
| TK #15 | 12-0137-11 | Grandview, ID | |
| TK #21 | 11-4134-1 | Marshall, MN | 2 |
| TK #22 | 11-4601-1 | Great Bend, KS | |
| TK #24 | 11-2909-2 | Carlisle, KY | |
| TK #28 | 11-0125-1 | Plainview, TX | 3 |
| TK #30 | 11-3169-2 | Las Animas, CO | |
| TK #33 | 11-3454-4 | Fairmont, MN | |
| TK #34 | 11-3452-2 | Fairmont, MN | 5 |
| TK #37 | 12-0370-1 | Cresco, IA | |
| TK #40 | 11-0012-1 | Gettysburg, SD | |
| TK #41 | 11-4378-2 | Gettysburg, SD | |
| TK #42 | 11-0141-1 | Parkston, SD | 4 |
| TK #44 | 11-0263-1 | Mesquite, NV | |
| TK #47 | 11-4312-1 | Sioux Center, IA | |
| 2336 | 2336 | Public WT (Control) | 6 |

Isolates stored at −80° C. were streak-plated onto Columbia+5% Sheep Blood agar plates (CSBA) (Becton Dickinson, Franklin Lakes, N.J.). The plates were incubated at 37° C. with 5% $CO_2$. After 18 hours of growth, the plates were washed with 2 mL DPBS and the resulting solution was diluted with additional DPBS and mixed 1:1 of culture and FBS (pre-warmed to RT) to obtain a final concentration of between $5\times10^8$ and $1\times10^9$ CFU/dose. After the FBS was added, the cultures were incubated for 5 min. at RT to up-regulate *H. somni* virulence factors, and then placed on ice.

Each group of ten, 18-20 g NSA: CF-1 mice (Harlan Sprague Dawley)/isolate were injected with 0.5 cc intraperitoneally (IP) with its assigned isolate. A control group of ten mice was given DPBS+FBS. Filter-tops were placed on the top of each of the mice cages with one cage equaling ten mice/isolate. The isolates were diluted and plated, and plates were incubated at 37° C. with 5% $CO_2$ for two days. Plates were counted and the actual CFU/dose was determined for each isolate. Additionally, five mice were injected SQ with isolates 2336 or TK #33, to determine if this route of administration would be a viable alternative (for assessing virulence) to the IP route. After challenge, mice were observed daily for mortality.

Most isolates yielded mid to upper 8 logs CFU/dose. The SQ method proved to be an unsuccessful method for challenging mice. Isolates TK #4, TK #24, TK #14, the controls, and 2336 resulted in the least percent mortality, while isolates TK #1, TK #2, TK #21, TK #28, and TK #30 resulted in the greatest percent mortality (Table 2).

TABLE 2

Percent mortality when 18-20 g mice were challenged with plate-grown isolates.

| Isolate # | Route | CFU/dose | % Mortality |
|---|---|---|---|
| TK #33 | SQ | $3.7\times10^8$ | 0 |
| Controls | IP | 0 | 0 |
| 2336 | IP | $1.7\times10^9$ | 0 |
| 2336 | SQ | $1.7\times10^9$ | 0 |
| TK #4 | IP | $7.6\times10^8$ | 10 |
| TK #14 | IP | $8.7\times10^8$ | 10 |
| TK #24 | IP | $5.5\times10^8$ | 10 |
| TK #34 | IP | $7.2\times10^8$ | 20 |
| TK #42 | IP | $5.9\times10^8$ | 20 |
| TK #5 | IP | $6.2\times10^8$ | 30 |
| TK #15 | IP | $7.5\times10^8$ | 30 |
| TK #33 | IP | $3.7\times10^8$ | 30 |
| TK #37 | IP | $7.3\times10^8$ | 30 |
| TK #41 | IP | $9.9\times10^8$ | 30 |
| TK #3 | IP | $8.6\times10^8$ | 40 |
| TK #22 | IP | $8.0\times10^8$ | 40 |
| TK #40 | IP | $9.9\times10^8$ | 40 |
| TK #44 | IP | $9.0\times10^8$ | 40 |
| TK #47 | IP | $7.0\times10^8$ | 40 |
| TK #1 | IP | $8.0\times10^8$ | 50 |
| TK #2 | IP | $8.7\times10^8$ | 50 |
| TK #28 | IP | $7.1\times10^8$ | 50 |
| TK #30 | IP | $4.8\times10^8$ | 50 |
| TK #21 | IP | $5.1\times10^8$ | 80 |

Challenge Model. Two studies were conducted to determine the ideal CFU/dose and challenge culture preparation for mice that would be larger in vaccination-challenge studies than in the previous study (i.e. taking into account the three weeks' growth between vaccination and challenge). For the first study, forty, 25-30 g NSA: CF-1 mice (Harlan Sprague Dawley) were used. *H. somni* Isolate TK #21 was streak-plated onto CSBA. After ~24 hours of growth at 37° C. with 5% $CO_2$ the isolate was lawned onto additional CSBAs and grown under the same conditions for 18-20 hours. Each plate was washed with 2 mL DPBS and the liquid was collected. Dilutions from the original plate wash were made to create two additional solutions varying in CFU/dose. Each dilution was mixed 1:1 with FBS to achieve final concentrations of challenge fluids ranging from low 8 logs to low 9 logs/dose. Control fluids were created with 1:1 DPBS and FBS. All FBS added cultures were incubated at room temp. for 5 min. and then placed on ice. Mice were challenged with 0.5 cc IP and monitored for mortality after challenge. The challenge cultures were diluted and plated to determine the ideal CFU/dose required for maximum mortality.

When the challenge culture TK #21 was grown on plates and mice were larger (25-30 g), to account for their expected size three-weeks post-vaccination, the greatest percent mortality was achieved at $5.7\times10^8$ CFU/dose (Table 3).

TABLE 3

Percent mortality when 25-30 g mice were challenged with plate-grown isolates.

| Group | Isolate | CFU/dose | % Mortality |
|---|---|---|---|
| 1 | TK #21 | $1.6 \times 10^9$ | 9.1 |
| 2 | TK #21 | $5.7 \times 10^8$ | 27.3 |
| 3 | TK #21 | $4.2 \times 10^8$ | 20 |
| 4 | Control | 0 | 0 |

A final challenge study was conducted with thirty, 25-30 g NSA: CF-1 mice (Harlan Sprague Dawley) to compare the difference between growing the challenge culture on plates (as is commonly done in the literature) or in broth. Similar as above, isolate TK #21 was removed from frozen storage and lawned onto additional plates. For the broth culture, a plate was washed with 2 mL Columbia broth and 50 µL was added to 25 mL pre-warmed Columbia broth. The culture was shaken vigorously after the culture wash was added and then placed on a shaker set to 37° C. and 250 rpm. Growth was monitored and the culture was stopped when we estimated the final challenge culture, with all fluids added, would contain mid-8 logs/dose. Also, a challenge culture was prepared by plate washing as above, with the culture diluted with DPBS to about the same concentration as the broth culture. Both the broth and plate cultures were mixed 1:1 with FBS and incubated for 5 min. at room temp. prior to being placed on ice. Eleven mice/method were challenged with 0.5 cc IP of the plate wash or the broth and 10 mice served as controls given a mixture of equal parts Columbia broth and DPBS, which was then mixed 1:1 with FBS. Mice were monitored for mortality post-challenge and dilutions and plating was completed to determine CFU/dose.

Greater mortality of 25-30 g mice occurred when mice were challenged with isolate #21 grown in broth compared to the same isolate grown on plates (Table 4). This result was unexpected, particularly considering the literature guided the skilled person away from growing *H. somni* in broth for use in a virulent challenge study (Berghaus et. al., 2006; Geertsema et. al., 2008; Gershwin et. al., 2005).

TABLE 4

| Percent mortality when 25-30 g mice were challenged with plate/broth-grown isolates. | | | |
|---|---|---|---|
| Method of Growth | Isolate | CFU/dose | % Mortality |
| Plates | TK #21 | $5.3 \times 10^8$ | 36.4 |
| Broth | TK #21 | $4.8 \times 10^8$ | 54.5 |
| — | Controls | — | 0 |

One hundred thirty NSA: CF-1 mice, 18-20 g were purchased from Harlan Sprague Dawley. Five *H. somni* isolates (TK #42, TK #14, TK #4, TK #24, and TK #34) were selected from the previous studies as vaccine candidates. These isolates were removed from storage and streaked onto CSBA where they were incubated for ~24 hours at 37° C. and 5% $CO_2$. The isolates were transferred to new CSBAs and lawned onto the plate surface where they were allowed to grow for –18 hours. The plates were washed with 2 mL Columbia broth. For isolates TK #42 and TK #34, 100 μL of plate wash was added to 25 mL of Columbia broth, and for isolates TK #4, TK #14, and TK #24, 50 μL of plate wash was added to 25 mL Columbia broth, based on previous studies involving the growth of these isolates.

The cultures were incubated at 37° C. and 200 rpm. Growth of the isolates was monitored and cultures were removed from incubation and diluted with Columbia broth to contain approximately $1\times10^8$ CFU/dose and a 1:10 dilution of this was made to make another vaccine estimated at $1\times10^7$ CFU/dose, for each isolate. A control group was vaccinated with sterile Columbia broth and another control group was vaccinated with the commercially available SOMUBAC® (Zoetis, inactivated *Histophilus* vaccine, adjuvanted with aluminum hydroxide, Kalamazoo, Mich.).

Each vaccine was maintained on ice after it was prepared and each group included 10 mice, with the exception of the Columbia Control group which included 6 mice. The vaccine was delivered SQ as 0.5 cc. After vaccination, the vaccines were diluted and plated to determine actual CFU/dose and mice were monitored daily for adverse reactions and/or death. Endotoxin involved in each vaccine was determined with the Limulus Amebocyte Lysate kit (Lonza, Allendale, N.J.).

Nineteen days after vaccination, mice were challenged with *H. somni* isolate TK #21. The wildtype was prepared for growth in broth similar as above, with the exception that 150 μL of plate wash was used to inoculate each of 2 flasks containing 75 mL pre-warmed Columbia broth each. The flasks were incubated at 37° C. and 250 rpm. The culture was removed from incubation, diluted, and mixed 1:1 with room temperature FBS to contain mid-8 logs/dose. The culture was incubated with the FBS at room temperature for 5 min. and placed on ice. The challenge product was dilution plated prior-to- and post-challenge to determine if the CFU/dose matched our estimate. Mice were administered 0.5 cc IP of the challenge culture and monitored daily for death.

Mice vaccinated with SOMUBAC® (Zoetis, inactivated *Histophilus* vaccine, adjuvanted with aluminum hydroxide), and isolates TK #34 and TK #22 at 8 logs, developed red injection site reactions. All isolates, with the exception of TK #22, provided some protection to mice prior to challenge, in comparison to the control group. Isolate TK #4 was effective at both vaccine doses, however, isolate TK #34 was best at 8 logs and isolates TK #24 and TK #42 were best at 7 logs. At both doses, isolate TK #14 provided some protection but less than the others (Table 5). Isolates TK #24 at 8 logs and TK #42 at 8 logs had one mouse of 10 die after vaccination, prior to challenge.

TABLE 5

| The percent mortality in mice vaccinated with a low virulence isolate and challenged with a high virulence isolate. | | | | |
|---|---|---|---|---|
| Isolate | Vaccine CFU/Dose | Vaccine EU/dose* | Challenge CFU/dose | % Mortality |
| TK #4 | $1.8 \times 10^7$ | — | $5.1 \times 10^8$ | 10 |
| TK #4 | $1.8 \times 10^8$ | 31,559 | $5.1 \times 10^8$ | 20 |
| TK #14 | $1.8 \times 10^7$ | — | $5.1 \times 10^8$ | 40 |
| TK #14 | $1.8 \times 10^8$ | 30,287 | $5.1 \times 10^8$ | 40 |
| TK #22 | $1.3 \times 10^7$ | — | $5.1 \times 10^8$ | 60 |
| TK #22 | $1.3 \times 10^8$ | 54,451 | $5.1 \times 10^8$ | 80 |
| TK #24 | $1.3 \times 10^7$ | — | $5.1 \times 10^8$ | 10 |
| TK #24 | $1.3 \times 10^8$ | 38,372 | $5.1 \times 10^8$ | 33 |
| TK #34 | $1.6 \times 10^7$ | — | $5.1 \times 10^8$ | 40 |
| TK #34 | $1.6 \times 10^8$ | 28,107 | $5.1 \times 10^8$ | 0 |
| TK #42 | $1.3 \times 10^7$ | — | $5.1 \times 10^8$ | 10 |
| TK #42 | $1.3 \times 10^8$ | 33,648 | $5.1 \times 10^8$ | 33 |
| SOMUBAC ® | — | — | $5.1 \times 10^8$ | 10 |
| Control | 0 | 2,307 | $5.1 \times 10^8$ | 67 |

*EU/dose = Endotoxin units/dose; EU/dose was only determined for the 8 log vaccines.

Example 2

H. somni Calf Challenge

Prior to testing the vaccine candidates, a calf challenge model had to be developed. For this study, twenty Holstein bull calves were used. Calves were challenged at 54 days-of-age using either isolate TK #21 or 153-3 (acquired from calves with confirmed clinical disease due to *H. somni*). The challenge culture was prepared in broth similar to above. To estimate the CFU/dose of the challenge culture, a previously established standard curve ($y=-5\times10^{-8}x+92.017$ ($x$=CFU/mL and y=% T (540 nm)) was used to determine the dilutions needed to achieve a final challenge concentration of ~$2.5\times10^8$ and $2.5\times10^9$ CFU/dose for each isolate. The culture was diluted with EBSS followed by the addition of a 1:1 ratio of FBS after which the cultures were incubated for 5 min. at room temp. The challenge cultures were placed on ice along with additional EBSS for chasing the challenge dose. For each of 4 calves per isolate and dose, 20 cc of challenge was administered trans-tracheally and was chased into the lungs with 60 cc of EBSS. Four animals remained as non-challenged controls, which were given 1:1 EBSS and FBS. The challenge culture was diluted and plated prior-to- and post-challenge to determine actual CFU administered. Clinical signs were rated and recorded daily by the same person as follows:

TABLE 6

Calf Challenge Clinical Signs Rating Criteria

| Rating | Criteria |
| --- | --- |
| | Attitude |
| 0 | Normal |
| 1 | Depressed |
| 2 | Moderately Depressed |
| 3 | Severely Depressed |
| | Anorexia |
| 0 | Normal |
| 1 | Little motivation to eat |
| 2 | No motivation to eat |
| 3 | No motivation to eat or interact → Humanely Euthanize |
| | Respiration Rate |
| 0 | Normal |
| 1 | Increased Respiration Rate |
| 2 | Labored Breathing |
| 3 | Labored Breathing and Wheezing |
| | Nasal Discharge |
| 0 | Normal |
| 1 | Small amount of unilateral discharge |
| 2 | Bilateral, excessive mucus discharge |
| 3 | Thick bilateral discharge |
| | Cough |
| 0 | Normal |
| 1 | Single Cough |
| 2 | Occasional spontaneous cough or repeated coughs |
| 3 | Repeated spontaneous coughs |
| | Ability to Rise or Walk |
| 0 | Normal |
| 1 | Rise with enticement and motivated to walk |
| 2 | Rise with enticement and no motivation to walk |
| 3 | No motivation to rise/walk → Humanely Euthanize |

The total clinical score was calculated for each animal by summing the ratings determined for each category. If an animal was found dead, or met the criteria of euthanasia, a necropsy was performed and the lungs removed. An attending veterinarian rated the lungs for % surface area lesions, and tissues were subjected to analysis. After 4 days, the remaining animals were euthanized and necropsied as above. Lung lesions were arcsine-transformed and analyzed using the "JMP Fit Y by X" function and means were separated with Student's t.

Twenty-four Holstein bull calves were divided into five pens containing five animals each for vaccination and 4 animals to serve as non-vaccinated controls. In addition, four animals from the challenge model's non-challenged group were kept alive given the calf vaccination-challenge study was scheduled to be challenged the following week. They were kept in a separate pen. These animals, referred to as controls from challenge model, were an additional experimental control to see if being in the same barn but not the same pen as challenged animals could affect the results when these animals were challenged. Vaccines were prepared as for mice using isolates TK #28, TK #42, TK #4, and TK #34. The vaccine cultures were prepared similarly to the above challenge culture without the addition of FBS. The vaccines were estimated to contain $5\times10^8$ CFU/dose and a dose was 2 cc, 1 cc administered in each calf nostril.

The vaccines were diluted and plated prior-to- and post-vaccination to determine the actual CFU/dose. Animal health was monitored post-vaccination. Nasal swabs and blood samples were collected from animals on day −17 (one day after arrival), day 0 (date of vaccination, calf age=35 days-old), day 14, day 21, and day 33 (date of challenge). Nasal swabs were submitted to the Newport Laboratories Diagnostic Lab for bacterial culture and blood samples were maintained for possible serology. All animals with the addition of the 4 control animals from the challenge model study, were challenged the same as above with an estimated $5\times10^9$ CFU/dose. Clinical signs, necropsies, lung lesions, bacterial culture, *Mycoplasma* PCR, and statistics were carried out as above with total clinical score and lung lesions also analyzed with JMP Fit Y by X.

For the challenge study, the actual plated CFU/dose was very close to the estimated $2.5\times10^9$ or $2.5\times10^8$ CFU/dose that was predicted. The animals challenged with isolate TK #21 were given $3.9\times10^9$ CFU/dose for the 9 log group and $2.9\times10^8$ CFU/dose for the 8 log group. The animals challenged with isolate 153-3 were given $1.8\times10^9$ CFU/dose for the 9 log group and $1.7\times10^8$ CFU/dose for the 8 log group.

More clinical signs of disease were observed for animals challenged with isolate TK #21 at 9 logs than any other challenge group (Table 7). In addition, more severe lung lesions were observed for animals challenged with isolate TK #21 than any other challenge group (FIG. 1). The majority of calves that had pneumonic lesions had *H. somni* recovered from the lung tissue. Throughout the study, *P. multocida* was recovered from the nasal swabs and the lung tissue, but did not appear to be a contributing cause of the disease symptoms, as animals did not show clinical signs of pneumonia until post-challenge. Also, many of the animals were confirmed positive or suspect for *M. bovis* in the lung tissue. As expected, no *M. bovoculi* was detected.

TABLE 7

The average sum of clinical signs rated during the challenge model study.

| Isolate | Average Clinical Score* |
| --- | --- |
| 153-3 (9 logs) | 0.75 |
| 153-3 (8 logs) | 0.25 |
| Controls | 0.00 |
| TK #21 (9 logs) | 7.00 |
| TK #21 (8 logs) | 1.75 |

*From the last rating taken of the animals prior to death.

The actual concentration of bacteria used for vaccination was close to the estimated $5 \times 10^8$ CFU/dose. *H. somni* was recovered only after vaccination with the live bacteria from two to three animals at each of the nasal swab collection dates of day 14, day 21, and day 33 post-vaccination. The nasal swabs demonstrated that *H. somni* can remain viable in the nasal passages for 21-33 days if not more (Table 8).

TABLE 8

Bacteria concentration and endotoxin administered to calves vaccinated intranasally with isolates TK #28, TK #42, TK #4, and TK #34, and the number of *H. somni* isolates recovered from the vaccinated animals throughout the study.

| Vaccine Isolate | Actual CFU/dose administered | Endotoxin Units/mL | Nasal Swab Recovery (day) of recovery)* |
|---|---|---|---|
| TK #28 | $3.90 \times 10^8$ | 27,800 | 2 calves (d21) 1 calf (d33) |
| TK #42 | $4.40 \times 10^8$ | 31,700 | 1 calf (d14) |
| TK #4 | $7.80 \times 10^8$ | 25,800 | 1 calf (d21) |
| TK #34 | $6.20 \times 10^8$ | 42,000 | 2 calves (d14); 1 calf (d33) |
| Control | 0 | <10,000 | None |

Figure 2:
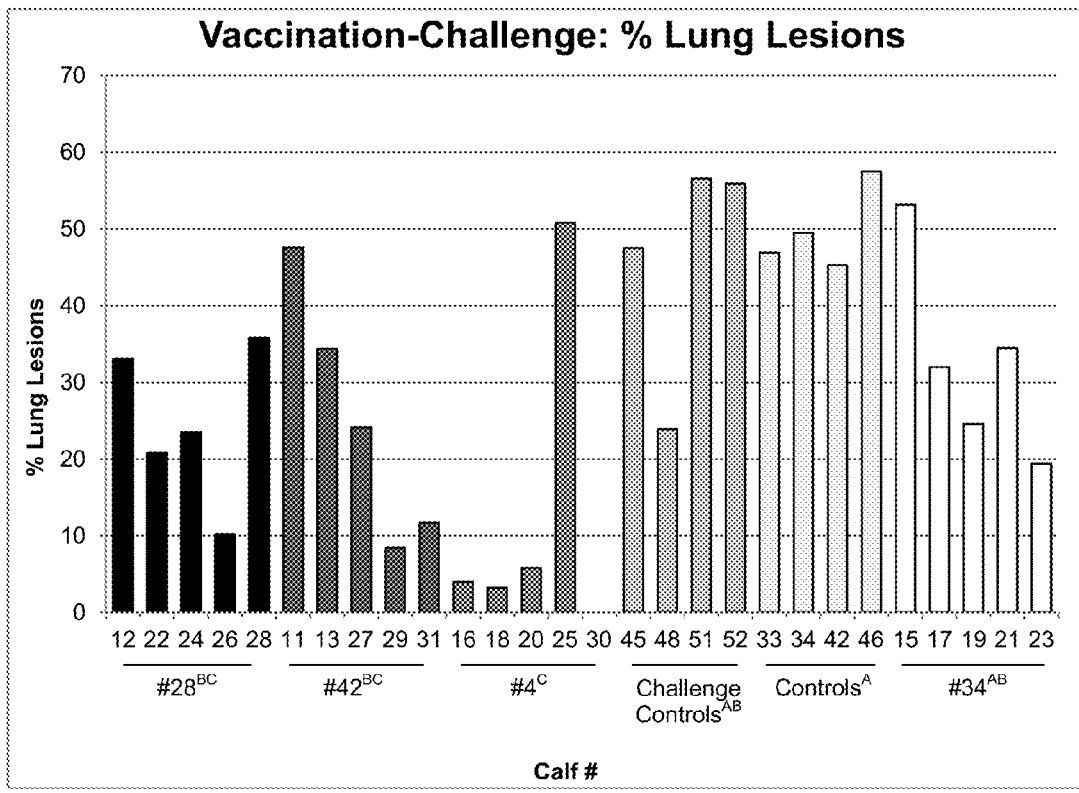
FIG. 2 shows the percent lung lesions observed for each calf in a vaccination-challenge study where the vaccine was administered intranasally. Bars of the same color represent the results for animals vaccinated with the same isolate. The vaccination isolate is listed below the bars, and all animals were challenged with the same challenge isolate. Groups followed by the same letter(s) are not significantly different according to Student's t performed on the arcsine transformed data.

The concentration of isolate TK #21 given to each calf at the time of challenge was $7.39 \times 10^9$ CFU/dose. The challenge was effective in determining the efficacy of the vaccines and to determine the most effective vaccine candidate. The clinical signs and percent of lung lesions show that isolate TK #4 was the most effective vaccine and isolate TK #34 was the least effective, while isolates TK #28 and TK #42 fall in between (Table 9; FIG. 2). *H. somni* was recovered from the lungs of all calves in the study, with the exception of 3 calves all of which were vaccinated with isolate TK #4, indicating that cause of death and/or disease for animals with lung lesions was attributable to the challenge isolate. During the study *P. multocida* was recovered from the nasal passages of some of the calves, increasingly as the study progressed. After challenge, *P. multocida* was recovered from the lung tissue of 9 of the 28 calves and *M. bovis* was detected in the lungs from three of the animals. Vaccination does not appear to correlate with the presence or absence of *P. multocida* or *M. bovis*. In addition, controls from the challenge model were not as susceptible to the challenge when compared to the control animals from this study. Since the challenge model controls were housed in the same barn as challenged animals, they may have acquired some immunity from previous exposure (Table 9).

TABLE 9

Clinical scores from animals vaccinated intranasally and challenged with *H. somni* wildtypes.

| Isolate | Average Clinical Score* |
|---|---|
| TK #28 | 5.80 BC |
| TK #42 | 6.00 BC |
| TK #4 | 1.40 C |
| TK #34 | 11.80 A |
| Controls | 10.50 AB |
| Controls from Challenge Model | 3.50 C |

*Is the average clinical scores from the last rating taken of the animals prior to death. Clinical scores with different letters are significantly different according to Student's t test.

Discussion.

As the data in the mouse model correlated well with the results obtained in calves, the inventors have provided a new and useful tool for selecting bovine vaccine/challenge candidates. Isolate TK #21 is an excellent challenge isolate due to its virulence and the reproducibility of the results. The ideal challenge dose appears to be around mid- to high-9 logs per dose in cattle when administered trans-tracheally.

When used as an intranasal vaccine, Isolate TK #4, was significantly protective against subsequent *H. somni* challenge (4 of 5 calves). Clinical signs and lung lesions were significantly different from non-vaccinates. Isolates TK #28 and TK #42 induced some protection in vaccinated calves, but the efficacy was lower (2 of 5 calves).

Example 3

Comparative Genomic Analysis of Virulent and Avirulent *H. somni* Isolates

As discussed above, various *H. somni* isolates had different levels of virulence in mice and cattle. One in particular, TK #4, showed promise as an intranasal cattle vaccine candidate (Example 2). In addition, TK #21 proved to be a highly virulent challenge isolate for cattle and mice, possessing a phenotype typical of challenge isolates used in the literature (2336 and HS91). To better understand the factors that affect this virulence and also to determine if recently acquired isolates remain similar to older isolates, eight *H. somni* isolates were submitted for whole genome sequencing. Four genes, a glycoside hydrolase family protein, a lipoprotein, a multicopper oxidase type 3, and a TetR family transcriptional regulator were found to be missing in TK #4, but present in TK #21. Also, the recently isolated *H. somni* lacked 211 to 316 genes present in 2336, a wildtype isolated in 1985. HS91, an isolate from 1991, lacked only 15 genes when compared to 2336. The data suggests that the genotype of TK #4 contributes to its avirulent phenotype, and that there is genetic drift within the *H. somni* population over time. The results demonstrate a genetic explanation for the attenuation of TK #4 and the need for current vaccine and challenge isolates to maintain efficacy in response to natural genetic drift.

To understand the genetic and molecular basis for the differential virulence a 9-way comparative genome analysis was carried out between TK #4, TK #21, TK #34, TK #28, TK #42, HS91, 2336 (a highly virulent strain, at least according to the literature), 129PT (a known avirulent strain in GenBank), and 153-3 (a moderately virulent strain), against GenBank isolate 2336. This analysis will also improve our understanding of possible genetic drift, and delineate genes involved in the virulence/avirulence mechanism.

Material and Methods

Sample Preparation for Sequencing

Eight *H. somni* isolates were identified as a diverse set of isolates that could be valuable in whole genome sequencing (Table 10). These isolates were from a number of locations, had a broad range of virulence, and were isolated from animals in different years. All these isolates were grown in Columbia broth (BD Ref#294420; Lot#0292713, Franklin Lakes, N.J.) and after growth, 10% glycerol was added to freeze the cultures in cryogenic vials (Fisher Scientific Cat.#10-500-26, Waltham, Mass.) at Newport Laboratories Research and Development facility (Worthington, Minn.) in a −80° C. freezer. The isolates were removed from the freezer and streak-plated onto Columbia Sheep Blood Agar plates (CSBA) (BD Ref#22165/221263; Lot#2227132 2012 11 13, Franklin Lakes, N.J.). The plates were incubated overnight at 37° C. with 5% $CO_2$. After 24-26 hours, the plates were removed from the incubator and used to lawn additional CSBA for growth overnight at 37° C. and 5% $CO_2$. After 16-18 hours of incubation the plates were washed with 2 mL pre-warmed Columbia broth with 100 μL or 150 μL used to start broth cultures of 25 mL Columbia broth for each of the cultures, using one flask for each inoculum amount. The broth cultures were shaken at 200 rpm and percent transmittance (% T)(540 nm) was monitored until the cultures reached 15-20% T. The broth cultures were removed from the incubator, pelleted three times in the same microcentrifuge tube by spinning 1.5 mL of culture each time for 2 min. at 15,000 rpm, and genomic DNA was isolated using a Bacterial Genomic DNA Purification Kit (Edge Biosystems, Gaithersburg, Md.), following the manufacturer's recommendation with slight modification. DNA was extracted in triplicate, from the triplicate spin pellets of each culture. A modification to the recommended DNA extraction process was the DNA was resuspended in 100 μL of TE and it was incubated for 15 min. at 37° C. to promote dissolving the DNA pellet without shearing the DNA. The three extractions were then pooled, compared on a 1% agarose gel, and quantified and purity checked on a Nanodrop. DNA amounts were calculated in order to provide the required total DNA for sequencing at the University of Idaho core facility (Moscow, Id.).

Then, all isolate reads were filtered for quality with the Illumina TruSeq adapters using SeqyClean, which is a read cleaning program developed at the University of Idaho (available on its website). This program removed the sequencing adapters and low quality reads which contained 5 or more bases with a Q-value <20, thus eliminating error during base reads and increasing accuracy.

Read Mapping

The genomic DNA results were mapped against 2336 in the NCBI database, Accession #CP000947 using bowtie2 default parameters. Filtering using a custom script for MAPQ <10 was used to remove multiply mapped reads. It is expected that identical isolates have an alignment rate >95%.

Gene Coverage

Samtools was used to calculate mapping coverage for each position against the 2336 reference. This was used to calculate the percentage of bases that had coverage for each gene. Genes that contained less than 80% of bases were called absent for that respective isolate. Two analyses were conducted on missing genes against 2336. The first compared HS91 (in a similar era as 2336), TK #21, TK #4, 153-3, and 129PT. The second compared TK #34, TK #42, 2336 (to confirm our 2336 matched the database), TK #28, and 129PT.

Pathogenicity Islands (PIs) and Integrative and Conjugative Elements (ICEs)

The results of the entire genome sequencing of HS91, TK #21, TK #4, 153-3 and 129PT were compared to 2336.

TABLE 10

List of *H. somni* isolates used for comparative genomic analysis.

| Isolate Name | Case # | Location | Phenotype |
|---|---|---|---|
| TK #34 | 11-3452-2 | Fairmont, MN | Reduced mortality in mice, but unable to reduce pneumonia as a cattle vaccine |
| HS91 | NA | Ames, IA | Wildtype from 1991 |
| TK #21 | 11-4134-1 | Marshall, MN | Highly virulent to mice and calves in challenge studies |
| TK #42 | 11-0141-1 | Parkston, SD | Had reduced virulence in mice and offered some protection as a mouse and cattle vaccine |
| 2336 | NA | Dr. Briggs | Industry standard for virulent *H. somni*; however, we found challenge inconsistency making us question age and number of passages |
| TK #28 | 11-0125-1 | Plainview, TX | Offered some protection to cattle |
| TK #4 | 12-0137-4 | Grandview, ID | Reduced virulence in mice, protected mice and cattle from challenge |
| 153-3 | NA | Worthington, MN | Wildtype recently obtained and seemed to be responsible for killing calves. In a calf challenge titration study it was not as virulent as TK #21. |

Filtering High Quality Reads and Sequence Coverage

To compare 129PT from the NCBI database, Accession #CP000436, against the 2336 Accession #CP000947, a similar approach to the field isolates needed to be used. Therefore, pseudo-reads were generated from 129PT with the ART read simulation software (hypertext transfer protocol://www.niehs.nih.gov/research/resources/software/biostatistics/art/). ART was run with the following command line: art_illumina −i Hs129PT.fasta −p −l250 −f 60 −m 500 −s 10 −na −o Hs129PT_sim, which equates to −p=paired, −l=25obp, −f=6ox coverage, −m=mean size of DNA fragments, −s=10 standard deviation of DNA fragment size.

Pathogenicity islands (PIs) and Integrative Conjugative Elements (ICEs) were searched for based on the presence of flanking signature sequences like recombinases, integrases, transposases, helicases, and phage repeats. Genomic regions containing a cluster of these putative signature sequences were identified as potential PIs or ICEs.

Results

The cleaned sequences had an approximate coverage of 100× for all isolates. The extent of the coverage gives us confidence in the quality of the called bases (Table 11).

TABLE 11

Quality of the raw reads and the estimated base coverage for each sequenced isolate.

| Library | PE Reads | Sequenced Bases | Estimated Raw Coverage | Cleaned PE Reads | Bases Kept After Cleaning | Estimated Cleaned Coverage |
|---|---|---|---|---|---|---|
| TK #34 | 454,197 | 235,274,046 | 103.93 | 460,095 | 210,850,732 | 93.14 |
| HS91 | 554,783 | 287,377,594 | 126.94 | 527,851 | 243,734,387 | 107.66 |
| TK #21 | 583,750 | 302,382,500 | 133.57 | 541,644 | 249,871,771 | 110.37 |
| TK #42 | 527,632 | 273,313,376 | 120.73 | 493,941 | 228,248,524 | 100.82 |
| 2336 | 848,512 | 439,529,216 | 194.15 | 809,986 | 378,965,750 | 167.40 |
| TK #28 | 544,568 | 282,086,244 | 124.60 | 520,290 | 241,511,214 | 106.68 |
| TK #4 | 606,064 | 313,941,152 | 138.68 | 570,358 | 261,675,306 | 115.59 |
| 153-3 | 463,065 | 239,867,670 | 105.96 | 441,209 | 202,578,292 | 89.48 |

The alignment revealed differences between the isolates and the reference strain. The GenBank 2336 isolate was 99.67% identical to the 2336 genome sequenced by Newport Labs, indicating the validity and accuracy of our map-based comparison between genomes. From there comparisons on similarities of the other isolates to 2336 were made with the second highest similarity to HS91. Also, the commensal 129PT (Accession #CP000436) in the NCBI database was aligned with the database's 2336 as a reference comparison (Table 12).

TABLE 12

The percentage of the sequencing data that aligned with the GenBank 2336 Accession # CP000947. Isolates are listed from highest to lowest percent alignment rate.

| Isolate | Alignment Rate (%) |
|---|---|
| HS91 | 99.71 |
| 2336 | 99.67 |
| 153-3 | 96.11 |
| TK #34 | 92.11 |
| TK #4 | 91.30 |
| TK #21 | 88.35 |
| 129PT* | 87.92 |
| TK #42 | 83.84 |
| TK #28 | 83.33 |

*Accession # CP000436.

Among the isolates, 129PT lacked many virulence and virulence-associated genes in comparison to the 2336 wildtype. The more recently acquired isolates lacked more total genes than the older isolates, when compared to the 2336 wildtype (Table 13).

TABLE 13

The number of genes estimated to be present or absent for each isolate sequenced in comparison to 2336 Accession # CP00947 in the NCBI database.

| Isolate | Genes Present | Genes Absent |
|---|---|---|
| 129PT* | 1593 | 472 |
| TK #34 | 1749 | 316 |
| TK #4 | 1758 | 307 |
| TK #21 | 1840 | 225 |
| TK #42 | 1848 | 217 |
| 153-3 | 1851 | 214 |
| TK #28 | 1854 | 211 |
| 2336 | 2048 | 17 |
| HS91 | 2050 | 15 |

*Accession # CP000436.

When comparing the genes that are absent in the first and second analyses relative to 2336, 129PT, the commensal, lacked more of those genes associated with pathogenicity and/or virulence than any other compared isolate. In total 129PT lacked 44 of the 47 total missing genes compiled from HS91, TK #21, TK #4, 153-3, and 129PT (Table 14). It also lacked 44 of the 47 total missing genes compiled from TK #34, TK #42, 2336, TK #28, and 129PT (Table 15). Isolate 2336 was found to lack only one identified pathogenicity-associated gene present in the NCBI database. This gene is a YadA domain-containing protein (Table 15).

The vaccine candidate, TK #4 lacked a total of 23 of the possible 47 absent genes from the isolates analyzed. This candidate lacked the attachment and adhesion genes of hemagglutinin/hemolysin, YadA domain-containing proteins (a total of 5 repeats missing), and a hemagglutinin domain-containing protein. TK#4 also lacked a transferrin binding protein (for iron uptake) and two isoforms of multicopper oxidase type 3 which provide the ability to uptake metals stored in the host. Genes responsible for host colonization such as glycoside hydrolase family protein (nasopharnyx colonization) and peptidase S8/S53 subtilisin kexin sedolisin were also missing from TK #4. Also, genes were missing that are responsible for drug resistance or response to stressors including two isoforms of a TetR family transcriptional regulator, acyltransferase 3, two isoforms of a MarR family transcriptional regulator, small multidrug resistance protein, the MarR family transcriptional regulator, and a stress-sensitive restriction system protein. Lastly, TK #4 lacked some genes that impact the pathogen's ability to evade host defenses such as lipooligosaccharide sialyltransferase, lipoprotein, and the Abi family protein (which is involved in self-immunity from bacteriocins) (Table 14).

In comparison to 2336, the highly pathogenic TK #21 also lacked similar virulence genes found to be missing in TK #4 (19 of the 23 missing TK #4 genes), with the exception of glycoside hydrolase family protein, lipoprotein, one isoform of multicopper oxidase type 3, and one isoform of the TetR family transcriptional regulator. The only gene that TK #21 lacked that TK #4 had was one repeat of the YadA domain-containing protein (Table 14).

HS91 was highly similar to 2336 and equally virulent according to published literature. None of the virulence or virulence-associated genes that could potentially play a role in pathogenesis was found to be missing in HS91 (Table 14).

Isolate 153-3 lacked many of the potential virulence genes found to be missing in TK#4 (14 of the 23 missing in TK #4), but there were some additional genes missing that were present in TK #4 (23 missing out of a total 47 identified across all isolates). In addition to TK #4, 153-3 lacked filamentous hemagglutinin outer membrane protein, adhesin, 10 repeats of the YadA domain-containing protein (compared to 5 with TK #4), glycosyl transferase family protein, and acetyltransferase. Genes that TK #4 lacked but were present in 153-3 were stress-sensitive restriction system protein, hemagglutinin domain-containing protein, glycoside hydrolase family protein, lipooligosaccharide sialyltransferase, Abi family protein, lipoprotein, one isoform of the multicopper oxidase type 3, one isoform of the TetR family transcriptional regulator, and peptidase S8/S53 subtilisin kexin sedolisin (Table 14).

The three recent isolates from the second analysis had more missing genes than older isolates. TK #34 lacked the most genes of the recent isolates, 22 out of 47. These genes included filamentous hemagglutinin outer membrane protein, hemagglutinin/hemolysin-like protein, adhesin, stress-sensitive restriction system, 6 repeats of the YadA domain-containing protein, transferrin binding protein, two isoforms of a hemagglutinin domain-containing protein, glycoside hydrolase family protein, TetR family transcriptional regulator, lob1 protein, two isoforms of the MerR family transcriptional regulator, multicopper oxidase type 3, small multidrug resistance protein, MarR family transcriptional regulator, and peptidase S8/S53 subtilisin kexin sedolisin. Of the 22 genes missing in TK #34, TK #42 was found to lack 12. These included: hemagglutinin/hemolysin-like protein, 5 repeats of the YadA domain-containing protein, one isoform of the TetR family transcriptional regulator, two isoforms of the MerR family transcriptional regulator, one isoform of multicopper oxidase type 3, small multidrug resistance protein, and MarR family transcriptional regulator. In addition to the 12 genes also absent with TK #34, TK #42 also lacked one repeat of the YadA domain-containing protein, glycosyl transferase family protein, virulence associated protein D (VapD), acyltransferase 3, lipoprotein, another isoform of multicopper oxidase type 3, and another isoform of the TetR transcriptional regulator. All the genes absent in TK #42 were also absent in TK #28, with no exceptions (Table 15).

TABLE 14

Genes involved in virulence that are missing in one or more of the analyzed genomes of HS91, TK #21, TK #4, 153-3, and 129PT, when compared to 2336 (Accession # CP00947).

| NCBI Gene # | Missing from? | Gene Name | Gene Function |
|---|---|---|---|
| HSM_0052 | 129PT | Outer membrane protein transport protein P1 | Can involve porins involved in transport of immunogenically important proteins and host evasion |
| HSM_0077 | 153-3 & 129PT | YadA domain-containing protein | Promotes pathogenicity and virulence in host cells through cell adhesion via a collagen binding outer-membrane protein |
| HSM_0164 | 129PT | Glycosyl transferase family protein | Involved in transferring a sugar moiety onto an acceptor, responsible for generating important virulence factors such as lipooligosaccharides (Kahler et. al. 1996) |
| HSM_0268 | 153-3 & 129PT | Filamentous hemagglutinin outer membrane protein | Mediates adherence to epithelial cells, macrophages and is required for tracheal colonization |
| HSM_0270 | TK #21, TK #4, 153-3, & 129PT | Hemagglutinin/hemolysin-like protein | Surface glycoprotein responsible for bacterial attachment to and penetration of host cells |
| HSM_0274 | 153-3 & 129PT | Adhesin | Involved in cell attachment |
| HSM_0338 | TK #21, TK #4, 153-3, & 129PT | YadA domain-containing protein | Promotes pathogenicity and virulence in host cells through cell adhesion via a collagen binding outer-membrane protein |
| HSM_0346 | 153-3 & 129PT | YadA domain-containing protein | Promotes pathogenicity and virulence in host cells through cell adhesion via a collagen binding outer-membrane protein |
| HSM_0377 | TK #21, TK #4, 153-3, & 129PT | YadA domain-containing protein | Promotes pathogenicity and virulence in host cells through cell adhesion via a collagen binding outer-membrane protein |
| HSM_0394 | 153-3 & 129PT | YadA domain-containing protein | Promotes pathogenicity and virulence in host cells through cell adhesion via a collagen binding outer-membrane protein |
| HSM_0598 | TK #21, TK #4, and 129PT | Stress-sensitive restriction system protein | Under stress it can allow bacteria to more easily pick up foreign DNA, such as phage DNA (Schäfer et. al. 1994) |
| HSM_0695 | 129PT | Alkaline phosphatase | Promotes biofilm formation |
| HSM_0708 | TK #21, TK #4, 153-3, & 129PT | YadA domain-containing protein | Promotes pathogenicity and virulence in host cells through cell adhesion via a collagen binding outer-membrane protein |
| HSM_0749 | TK #21, TK #4 & 153-3 | transferrin binding protein | Makes it possible for the bacteria to acquire stored iron from the host, which can affect virulence |
| HSM_0844 | 129PT | YadA domain-containing protein | Promotes pathogenicity and virulence in host cells through cell adhesion via a collagen binding outer-membrane protein |
| HSM_0953 | TK #21 & TK #4 | Hemagglutinin domain-containing protein | Involved in bacterial adhesion |
| HSM_0975 | 129PT | Glycosyl transferase family protein | Involved in transferring a sugar moiety onto an acceptor, responsible for generating important virulence factors such as lipooligosaccharides (Kahler et. al. 1996) |
| HSM_0977 | 153-3 & 129PT | Glycosyl transferase family protein | Involved in transferring a sugar moiety onto an acceptor, responsible for generating important |

TABLE 14-continued

Genes involved in virulence that are missing in one or more of the analyzed genomes
of HS91, TK #21, TK #4, 153-3, and 129PT, when compared to 2336 (Accession # CP00947).

| NCBI Gene # | Missing from? | Gene Name | Gene Function |
|---|---|---|---|
| | | | virulence factors such as lipooligosaccharides (Kahler et. al. 1996) |
| HSM_0978 | 129PT | Glycosyl transferase family protein | Involved in transferring a sugar moiety onto an acceptor, responsible for generating important virulence factors such as lipooligosaccharides (Kahler et. al. 1996) |
| HSM_1089 | 129PT | Hemolysin activation/secretion protein-like protein | Involved in the lysis of red blood cells |
| HSM_1090 | 129PT | Filamentous hemagglutinin outer membrane protein | Can be involved in the secretion of adhesins that facilitate adhesion to the host or other cells, necessary for host colonization |
| HSM_1160 | TK #4 & 129PT | Glycoside hydrolase family protein | Can play a role in peptidoglycan degradation and also in colonization of the nasopharnyx and invasion of host epithelial cells |
| HSM_1191 | TK #21, TK #4, 153-3, & 129PT | TetR family transcriptional regulator | Involved in the transcriptional control of multidrug efflux pumps, pathways for the biosynthesis of antibiotics, response to osmotic stress and toxic chemicals, control of catabolic pathways, differentiation processes, and pathogenicity (Ramos et. al. 2005) |
| HSM_1212 | 129PT | hemagglutinin domain-containing protein | Involved in bacterial adhesion |
| HSM_1257 | TK #21, TK #4, 153-3, & 129PT | YadA domain-containing protein | Promotes pathogenicity and virulence in host cells through cell adhesion via a collagen binding outer-membrane protein |
| HSM_1426 | TK #21, TK #4, & 129PT | Lipooligosaccharide sialyltransferase | Affects the ornamentation on the lipooligosaccharide and impacts the pathogen's ability to evade host defenses |
| HSM_1448 | 129PT | Virulence-associated protein D (VapD) region | Toxin/antitoxin locus, can be involved in translation during stressful conditions, translation arrest would improve survival in the host and promote chronic mucosal infections (Daines et. al. 2004) |
| HSM_1484 | 153-3 & 129PT | YadA domain-containing protein | Promotes pathogenicity and virulence in host cells through cell adhesion via a collagen binding outer-membrane protein |
| HSM_1542 | 153-3 & 129PT | YadA domain-containing protein | Promotes pathogenicity and virulence in host cells through cell adhesion via a collagen binding outer-membrane protein |
| HSM_1571 | TK #21 & 129PT | YadA domain-containing protein | Promotes pathogenicity and virulence in host cells through cell adhesion via a collagen binding outer-membrane protein |
| HSM_1616 | TK #21, TK #4, & 129PT | Abi family protein | Involved in self-immunity to bacteriocins (Kjos et. al. 2010) |
| HSM_1624 | TK #21, TK #4, 153-3 & 129PT | Acyltransferase 3 | Drug resistance and other host evasion responses can be dependent on the presence of acyltransferases |
| HSM_1647 | 129PT | FhaB protein | Can have a role in host-cell binding and infection |
| HSM_1651 | 129PT | Filamentous hemagglutinin outer membrane protein | Can be involved in the secretion of adhesins that facilitate adhesion to the host or other cells, necessary for host colonization |
| HSM_1667 | 129PT | Lob1 protein | Involved in lipooligosaccharide biosynthesis for evading or delaying host recognition (Cox et. al. 1998) |
| HSM_1669 | 153-3 | Acetyltransferase | Involved in evading the host immune system, virulence, and drug resistance (Aubry et. al. 2011) |
| HSM_1714 | TK #4 & 129PT | Lipoprotein | Expressed on the cell surface and can be involved in host evasion and virulence |
| HSM_1726 | TK #4 & 129PT | Multicopper oxidase type 3 | Could be involved in Iron (II) acquisition in low oxygen environments from inflamed tissue, such as lung colonization of the host (Huston et. al. 2002) |
| HSM_1728 | TK #21, TK #4, 153-3, 129PT | MerR family transcriptional regulator | Transcriptional regulator via a suboptimal promoter that responds to stressors such as oxidative stress, heavy metals, or antibiotics (Brown et. al. 2003) |
| HSM_1730 | TK #21, TK #4, 153-3, 129PT | Multicopper oxidase type 3 | Could be involved in Iron (II) acquisition in low oxygen environments from inflamed tissue, such as lung colonization of the host (Huston et. al. 2002) |
| HSM_1734 | TK #4, 129PT | TetR family transcriptional regulator | Involved in the transcriptional control of multidrug efflux pumps, pathways for the biosynthesis of antibiotics, response to osmotic stress and toxic chemicals, control of catabolic pathways, |

TABLE 14-continued

Genes involved in virulence that are missing in one or more of the analyzed genomes of HS91, TK #21, TK #4, 153-3, and 129PT, when compared to 2336 (Accession # CP00947).

| NCBI Gene # | Missing from? | Gene Name | Gene Function |
|---|---|---|---|
| | | | differentiation processes, and pathogenicity (Ramos et. al. 2005) |
| HSM_1736 | TK #21, TK #4, 153-3 & 129PT | Small multidrug resistance protein | Drug efflux protein involved in antibiotic resistance (Alekshun and Levy, 2007). |
| HSM_1737 | TK #21, TK #4, 153-3 & 129PT | MarR family transcriptional regulator | Regulate activity of genes involved in antibiotic resistance, stress responses, virulence or catabolism of aromatic compounds (Perera and Grove, 2010) |
| HSM_1741 | TK #21, TK #4, 153-3 & 129PT | MerR family transcriptional regulator | Transcriptional regulator via a suboptimal promoter that responds to stressors such as oxidative stress, heavy metals, or antibiotics (Brown et. al. 2003) |
| HSM_1793 | TK #21, TK #4, 153-3 & 129PT | YadA domain containing protein | Promotes pathogenicity and virulence in host cells through cell adhesion via a collagen binding outer-membrane protein |
| HSM_1794 | 129PT | Glycosyl transferase family protein | Involved in transferring a sugar moiety onto an acceptor, responsible for generating important virulence factors such as lipooligosaccharides (Kahler et. al. 1996) |
| HSM_1889 | TK #21, TK #4, & 129PT | Peptidase S8/S53 subtilisin kexin sedolisin | Functions as a hydrolase, protease, and serine protease that help with initial colonization of the host |

TABLE 15

Genes involved in virulence that are missing in one or more of the analyzed genomes of TK #34, TK #42, 2336, TK #28, and 129PT, when compared to 2336 (Accession # CP00947 in the NCBI database).

| 2336 NCBI Gene # | Missing from? | Gene Name | Gene Function |
|---|---|---|---|
| HSM_0052 | 129PT | Outer membrane protein transport protein P1 | Can involve porins involved in transport of immunogenically important proteins and host evasion |
| HSM_0077 | TK #42, TK #28, & 129PT | YadA domain-containing protein | Promotes pathogenicity and virulence in host cells through cell adhesion via a collagen binding outer-membrane protein |
| HSM_0164 | 129PT | Glycosyl transferase family protein | Involved in transferring a sugar moiety onto an acceptor, responsible for generating important virulence factors such as lipooligosaccharides (Kahler et. al. 1996) |
| HSM_0268 | TK #34 & 129PT | Filamentous hemagglutinin outer membrane protein | Mediates adherence to epithelial cells, macrophages and is required for tracheal colonization |
| HSM_0270 | TK #34, TK #42, TK #28, & 129PT | Hemagglutinin/hemolysin-like protein | Surface glycoprotein responsible for bacterial attachment to, and penetration of, host cells |
| HSM_0274 | TK #34 & 129PT | Adhesin | Involved in cell attachment |
| HSM_0338 | 129PT | YadA domain-containing protein | Promotes pathogenicity and virulence in host cells through cell adhesion via a collagen binding outer-membrane protein |
| HSM_0346 | 129PT | YadA domain-containing protein | Promotes pathogenicity and virulence in host cells through cell adhesion via a collagen binding outer-membrane protein |
| HSM_0377 | 129PT | YadA domain-containing protein | Promotes pathogenicity and virulence in host cells through cell adhesion via a collagen binding outer-membrane protein |
| HSM_0394 | 129PT | YadA domain-containing protein | Promotes pathogenicity and virulence in host cells through cell adhesion via a collagen binding outer-membrane protein |
| HSM_0598 | TK #34 & 129PT | Stress-sensitive restriction system protein | Under stress it can allow bacteria to more easily pick up foreign DNA, such as phage DNA (Schäfer et. al. 1994) |
| HSM_0695 | 129PT | Alkaline phosphatase | Promotes biofilm formation |
| HSM_0708 | TK #34, TK #42, TK #28, & 129PT | YadA domain-containing protein | Promotes pathogenicity and virulence in host cells through cell adhesion via a collagen binding outer-membrane protein |

TABLE 15-continued

Genes involved in virulence that are missing in one or more of the analyzed genomes of TK #34, TK #42, 2336, TK #28, and 129PT, when compared to 2336 (Accession # CP00947 in the NCBI database).

| 2336 NCBI Gene # | Missing from? | Gene Name | Gene Function |
|---|---|---|---|
| HSM_0749 | TK #34 | Transferrin binding protein | Makes it possible for the bacteria to acquire stored iron from the host, which can affect virulence |
| HSM_0844 | 129PT | YadA domain-containing protein | Promotes pathogenicity and virulence in host cells through cell adhesion via a collagen binding outer-membrane protein |
| HSM_0938 | TK #34 | Hemagglutinin domain-containing protein | Involved in bacterial adhesion |
| HSM_0975 | TK #42, TK #28, & 129PT | Glycosyl transferase family protein | Involved in transferring a sugar moiety onto an acceptor, responsible for generating important virulence factors such as lipooligosaccharides (Kahler et. al. 1996) |
| HSM_0977 | 129PT | Glycosyl transferase family protein | Involved in transferring a sugar moiety onto an acceptor, responsible for generating important virulence factors such as lipooligosaccharides (Kahler et. al. 1996) |
| HSM_0978 | 129PT | Glycosyl transferase family protein | Involved in transferring a sugar moiety onto an acceptor, responsible for generating important virulence factors such as lipooligosaccharides (Kahler et. al. 1996) |
| HSM_1022 | TK #34 | YadA domain-containing protein | Promotes pathogenicity and virulence in host cells through cell adhesion via a collagen binding outer-membrane protein |
| HSM_1089 | 129PT | Hemolysin activation/secretion protein-like protein | Involved in the lysis of red blood cells |
| HSM_1090 | 129PT | Filamentous hemagglutinin outer membrane protein | Mediates adherence to epithelial cells, macrophages and is required for tracheal colonization |
| HSM_1160 | TK #34 & 129PT | Glycoside hydrolase family protein | Can play a role in peptidoglycan degradation and also in colonization of the nasopharnyx and invasion of host epithelial cells |
| HSM_1191 | TK #34, TK #42, TK #28, & 129PT | TetR family transcriptional regulator | Involved in the transcriptional control of multidrug efflux pumps, pathways for the biosynthesis of antibiotics, response to osmotic stress and toxic chemicals, control of catabolic pathways, differentiation processes, and pathogenicity (Ramos et. al. 2005) |
| HSM_1212 | TK #34 & 129PT | Hemagglutinin domain-containing protein | Involved in bacterial adhesion |
| HSM_1257 | TK #34, TK #42, TK #28, & 129PT | YadA domain-containing protein | Promotes pathogenicity and virulence in host cells through cell adhesion via a collagen binding outer-membrane protein |
| HSM_1426 | 129PT | Lipooligosaccharide sialyltransferase | Affects the ornamentation on the lipooligosaccharide and impacts the pathogen's ability to evade host defenses |
| HSM_1448 | TK #42, TK #28, & 129PT | Virulence-associated protein D (VapD) region | Toxin/antitoxin locus, can be involved in translation during stressful conditions, translation arrest would improve survival in the host and promote chronic mucosal infections (Daines et. al. 2004) |
| HSM_1484 | 129PT | YadA domain-containing protein | Promotes pathogenicity and virulence in host cells through cell adhesion via a collagen binding outer-membrane protein |
| HSM_1542 | TK #34, TK #42, TK #28, & 129PT | YadA domain-containing protein | Promotes pathogenicity and virulence in host cells through cell adhesion via a collagen binding outer-membrane protein |
| HSM_1571 | TK #34, TK #42, TK #28, & 129PT | YadA domain-containing protein | Promotes pathogenicity and virulence in host cells through cell adhesion via a collagen binding outer-membrane protein |
| HSM_1616 | 129PT | Abi family protein | Involved in self-immunity to bacteriocins (Kjos et. al. 2010) |
| HSM_1624 | TK #42, TK #28, & 129PT | Acyltransferase 3 | Drug resistance and other host evasion responses can be dependent on the presence of acyltransferases |
| HSM_1647 | 129PT | FhaB protein | Can have a role in host-cell binding and infection |
| HSM_1651 | 129PT | Filamentous hemagglutinin | Can be involved in the secretion of adhesins that facilitate adhesion to the host or other |

TABLE 15-continued

Genes involved in virulence that are missing in one or more of the analyzed genomes of TK #34, TK #42, 2336, TK #28, and 129PT, when compared to 2336 (Accession # CP00947 in the NCBI database).

| 2336 NCBI Gene # | Missing from? | Gene Name | Gene Function |
|---|---|---|---|
| | | outer membrane protein | cells, necessary for host colonization |
| HSM_1667 | TK #34 & 129PT | Lob1 protein | Involved in lipooligosaccharide biosynthesis for evading or delaying host recognition (Cox et. al. 1998) |
| HSM_1714 | TK #42, TK #28, & 129PT | Lipoprotein | Expressed on the cell surface and can be involved in host evasion and virulence |
| HSM_1726 | TK #42, TK #28, & 129PT | Multicopper oxidase type 3 | Could be involved in Iron (II) acquisition in low oxygen environments from inflamed tissue, such as lung colonization of the host (Huston et. al. 2002) |
| HSM_1728 | TK #34, TK #42, TK #28, & 129PT | MerR family transcriptional regulator | Transcriptional regulator via a suboptimal promoter that responds to stressors such as oxidative stress, heavy metals, or antibiotics (Brown et. al. 2003) |
| HSM_1730 | TK #34, TK #42, TK #28, & 129PT | Multicopper oxidase type 3 | Could be involved in Iron (II) acquisition in low oxygen environments from inflamed tissue, such as lung colonization of the host (Huston et. al. 2002) |
| HSM_1734 | TK #42, TK #28, & 129PT | TetR family transcriptional regulator | Involved in the transcriptional control of multidrug efflux pumps, pathways for the biosynthesis of antibiotics, response to osmotic stress and toxic chemicals, control of catabolic pathways, differentiation processes, and pathogenicity (Ramos et. al. 2005) |
| HSM_1736 | TK #34, TK #42, TK #28, & 129PT | Small multidrug resistance protein | Drug efflux protein involved in antibiotic resistance (Alekshun and Levy, 2007) |
| HSM_1737 | TK #34, TK #42, TK #28, & 129PT | MarR family transcriptional regulator | Regulate activity of genes involved in antibiotic resistance, stress responses, virulence or catabolism of aromatic compounds (Perera and Grove, 2010) |
| HSM_1741 | TK #34, TK #42, TK #28, & 129PT | MerR family transcriptional regulator | Transcriptional regulator via a suboptimal promoter that responds to stressors such as oxidative stress, heavy metals, or antibiotics (Brown et. al. 2003) |
| HSM_1793 | TK #34, TK #42, 2336, TK #28, &129PT | YadA domain-containing protein | Promotes pathogenicity and virulence in host cells through cell adhesion via a collagen binding outer-membrane protein |
| HSM_1794 | 129PT | Glycosyl transferase family protein | Involved in transferring a sugar moiety onto an acceptor, responsible for generating important virulence factors such as lipooligosaccharides (Kahler et. al. 1996) |
| HSM_1889 | TK #34 & 129PT | Peptidase S8/S53 subtilisin kexin sedolisin | Functions as a hydrolase, protease, and serine protease that helps with initial colonization of the host |

Seven Putative PIs or ICEs were Identified from the Whole Genome Compilation.

The first one is located between HSM_R0009 to approximately HSM_0254 (~28 kb), but no notable virulence, virulence-associated, or drug resistance genes appear to be present in this location. HS91 and 2336 contained all of the genes present; however, TK #21, TK #4, 153-3, 129PT, and TK #34 appear to lack the majority of the genes located in this PI or ICE. TK #42 and TK #28 have part of this first PI or ICE.

The second location was between HSM_0319 to HSM_0348 (~41 kb), and at this location there were two repeats of YadA domain-containing proteins, one which was lacking in TK #21, TK #4, 153-3, and 129PT and the other was missing in 153-3 and 129PT.

A third PI was located between HSM_0638 to HSM_0692 (~45 kb). Isolates 153-3, 129PT, and TK #34 lacked many of the genes in this potential PI or ICE; however, none were identified as putative virulence, virulence-associated, or drug resistance genes, because many of the genes in the PI were only identified as hypothetical proteins.

The fourth PI location was between HSM_0847 and HSM_0923 (~73 kb). Again no virulence factors were identified within this range; however TK #21, TK #4, 153-3, 129PT, and TK #34 lacked a majority of the genes found in this region.

The fifth PI location was between HSM_1115 and HSM_1167 (~51 kb). TK #4 lacks HSM_1129 to HSM_1146 and HSM_1149 to HSM_1167, this absent region includes a glycoside hydrolase family protein. Isolate 129PT lacks HSM_1131 to HSM_1167, and TK #34 lacks HSM_1129 to HSM_1144 and HSM_1149 to HSM_1167, but the other isolates have most of these genes present. There is also a two-component response regulator at HSM_1124 that can be involved in helping the bacteria sense and respond to a wide variety of environments. All of the sequenced isolates contain this two-component response regulator.

The sixth putative PI or ICE is from HSM_1615 to HSM_1719 (~101 kb). In this region, there is an Abi family protein, acyltransferase 3, FhaB protein, filamentous hemagglutinin outer membrane protein, Lob1 protein, acetyltransferase, and a lipoprotein. TK #21, TK #4, 153-3, 129PT, TK #28, TK #42, and TK #34 lack some of these (Tables 14 & 15), potentially contributing to their different levels of virulence.

The last potential PI or ICE is located at HSM_1860 to HSM_R0065 (~38 kb). One key gene that is missing from TK #21, TK #4, 129PT, and TK #34 in this region is the peptidase S8/S53 subtilisin kexin sedolisin, which is important for initial host colonization. There are other genes missing from TK #21, TK #4, 129PT, TK #34, TK #42, and TK #28, most of which are identified as hypothetical proteins or transposases. HS91, 153-3, TK #42, 2336, and TK #28 appear to have most or all this entire region intact.

Discussion

TK #4 appears to be sufficiently attenuated, while still capable of eliciting an adequate immune response, making the strain a strong vaccine candidate. TK #4 lacks some genes similar to other isolates acquired about the same year; however, some of the absent genes are unique to TK #4, including: a glycoside hydrolase family protein (GHFP), a lipoprotein (LP), a multicopper oxidase type 3, and a TetR family transcriptional regulator. Several genes, missing from both TK #4 and pathogenic isolates, may contribute to the attenuated phenotype, however, these genes do not appear to be necessary for avirulence.

On the other hand, two genes uniquely absent from TK #4, while present in pathogenic strains, glycoside hydrolase family protein and lipoprotein, appear to be necessary and sufficient for TK #4's attenuated phenotype.

A causal link between the absence of expression of these two genes—in TK #4—and the attenuated virulence is supported by previously published work, which indicates the GHFP and LP proteins play an important role in colonization and evasion of host defenses (Asgarali et. al. 2009; Garbe and Collin, 2010; Liu et. al. 2008; and Guzmán-Brambila et. al. 2012). Moreover, the data indicate that while TK #4 is not as attenuated as 129PT, the strain affords protection (from subsequent virulent challenge) to both cattle and mice.

TK #34 is also highly attenuated similar to TK #4; however, TK #4 is missing a greater number of genes involved in host evasion. TK #4 and TK #34 both lack various isoforms or repeats of hemagglutinin domain-containing proteins and YadA domain-containing proteins, respectively. TK #34 lacks a filamentous hemagglutinin outer membrane protein, adhesion, and the lob1 protein, which TK #4 has. TK #4 lacks a lipooligosaccharide sialyltransferase, Abi family protein, acyltransferase 3, lipoprotein, multicopper 3, and TetR transcriptional regulator that are present in TK #34. The results indicate that the combination of missing virulence factors contributes to a partially attenuated bacteria that is protective in mice and cattle (TK #4) or to a highly attenuated but not protective isolate for mice and cattle (TK #34). The data here alone indicate that a skilled person could not have predicted ahead of time which genes should be deleted to obtain a sufficiently attenuated, yet sufficiently protective, *H. somni* vaccine strain.

Finally, horizontal gene transfer appears not to have passed some resistance genes to this isolate, and a lack of other virulence factors appear to have attenuated the isolate sufficiently to render it incapable of causing disease. On the other hand, the presence of more virulence factors than a commensal strain makes TK #4 a strong vaccine candidate (i.e. the strain can survive long enough to stimulate the host humoral immune response and provide longer-term protection).

TK #21 was found to be a highly virulent isolate in mice and cattle. However, genetically, it was more similar to current isolates, TK #4 and 153-3 (less virulence relative to TK #21), while at the same time more divergent from other known virulent strains, 2336 and HS91. TK #21 did possess a, glycoside hydrolase family protein, a lipoprotein, one isoform of multicopper oxidase type 3, and one isoform of the TetR family transcriptional regulator that TK #4 lacked. These 4 genes may all contribute to the attenuation of TK #4. The most unique genes missing that were not found missing as different isoforms in TK #21, were glycoside hydrolase and a lipoprotein. These genes in combination appear to be necessary for causing the sufficient difference between a challenge isolate (has the genes) and a vaccine candidate (lacks the genes). TK #21 did lack a Yad A domain-containing protein that TK #4 had; however, it does not seem to contribute to lack of virulence. It seems that virulence associated with TK #21 is not due to its divergence from 2336, but instead to its subtle differences from TK #4.

The more recent isolates of TK #21, TK #4, 153-3, TK #34, TK #42, and TK #28 appear to be similar, but they are notably different from 2336 and HS91 (see Table 15). The data suggests that the *H. somni* population is evolving over time and that the generally accepted challenge isolate of 2336 may no longer be relevant to the *H. somni* gene pool calves are currently facing. This also provides evidence to support TK #4 as a vaccine candidate, since its genetic composition is highly relevant to currently circulated strains in the calf bovine respiratory disease complex. The alignment rate supports that HS91 and 2336 are very closely related, and that TK #21, TK #4, 153-3, TK #34, TK #42, and TK #28 are closely related. It also shows that the current isolates are genetically different from those isolated in the 1980-1990s. Also, when looking at gene absence, the more current isolates lack higher numbers of 2336 genes than HS91, and the current isolates also tend to lack similar genes. This implies that genomes are naturally drifting in *H. somni*. Also, since the current isolates represent different states within the U.S., it implies that the genetic drift seen here is representative of the current *H. somni* population in the U.S.

Overall, this data indicates that a combination of a number of genes may be required to make an isolate an effective vaccine or challenge candidate, and the loss of only a few genes can attenuate the candidate enough to save an animal versus take its life. This data also suggests, that the *H. somni* population does drift over time and that the industry needs to evolve in order to maintain relevant vaccines. The data strongly supports the importance of autogenous vaccines, as well as, periodic re-evaluation of commercial vaccine efficacy.

TABLE 16

The variants identified (with respect to 2336, accession #CP00947) for each isolate analyzed with "SAMTools mpileup."

| Sample | Total Variants | Filtered variants |
|---|---|---|
| 129PT | 22,040 | 21,733 |
| TK #34 | 23,386 | 23,179 |
| HS91 | 132 | 12 |
| HS91 ΔaroC | 1,481 | 1,343 |
| TK #21 | 25,840 | 25,157 |
| TK #42 | 21,833 | 21,677 |
| 2336 (Applicants' isolate) | 134 | 15 |
| TK #28 | 21,803 | 21,590 |
| TK #4 | 25,868 | 25,176 |

TABLE 16-continued

The variants identified (with respect to 2336, accession #CP00947) for each isolate analyzed with "SAMTools mpileup."

| Sample | Total Variants | Filtered variants |
|---|---|---|
| 153-3 | 21,260 | 20,750 |
| HS91 ΔnanPU | 1,468 | 1,330 |

In addition to many SNPs identified (Table 16), there were also numerous missing genes (Tables 17-23). The more recent isolates (TK #21, TK #4, 153-3, TK #34, TK #42, and TK #28) and 129PT had the most SNPs, while the HS91 wildtype, HS91 mutants, and 2336 had few to no SNPs for all virulence-associated genes. For the LOS biosynthesis or modification genes, the highest percentage SNPs were found in the glycosyl transferase and acetyltransferase genes in both analyses, and in lob2b of the group 2 analysis. Isolate 129PT lacked the most LOS biosynthesis or modification genes. For the adhesion, colonization, and biofilm formation genes, the most SNPs occurred in the YadA domain-containing proteins and the hemagglutinin domain-containing proteins. Many of the adhesion, colonization, and biofilm formation genes were missing in the recent isolates. Glycoside hydrolase in group 1 and in both groups some of the TonB-dependent receptors had the most SNPs for host invasion or metal uptake. Many of the stress-response, antibiotic resistance genes, and drug efflux genes were missing from most of the newer isolates. Of those that were present, the percentage of SNPs was fairly low with the exception of the TetR family transcriptional regulator in group 1.

For genes involved in LOS biosynthesis or modification, all isolates with the exception of 129PT had 1 indel in OMP transport protein P1. TK #21 and TK #34 had 1 and 2 indels, respectively, for lob2b. All recent isolates had 1 indel for pgmB, but the older isolates of HS91 and 2336 did not. TK #42 and TK #28 had 1 indel in a glycosyl transferase family protein, and they had 1 indel in lob2a. Isolate 129PT had an indel in neuA$_{HS}$.

In the group 1 analysis of non-synonymous indels for virulence-associated genes involved in adhesion, colonization, and biofilm formation, TK #21 and TK #4 had the most indels. These occurred in the YadA domain-containing proteins (26 total indels for TK #21 and 32 total indels for TK #4), filamentous hemagglutinin outer membrane proteins (6 total indels for TK #21 and 5 total indels for TK #4), and 1 indel for TK #21 in an adhesin. Isolate 153-3 also had some indels in group 1 but lacked the majority of the genes analyzed, somewhat similar to 129PT. Of those genes present with non-synonymous indels were YadA domain containing proteins (total of 6 indels), a filamentous hemagglutinin outer membrane protein (3 indels), and a hemagglutinin domain-containing protein (1 indel; Table 19). For the analysis on group 2 of the adhesion, colonization, and biofilm formation, isolates TK #34, TK #42, and TK #28 had the most indels. The indels were present in YadA domain-containing proteins (24 total indels for TK #34, 31 total indels for TK #42, and 31 total indels for TK #28), filamentous hemagglutinin outer membrane proteins (2 total indels for TK #34, 4 total indels for TK #42, and 4 total indels for TK #28) and 1 indel for a hemagglutinin domain-containing protein for TK #34. Also, 129PT had 7 indels for the YadA domain-containing proteins and 1 indel in a hemagglutinin domain-containing protein, although it lacked many of the genes analyzed. Lastly, HS91 ΔaroC and HS91 ΔnanPU had 3 and 2 total indels, respectively, for a filamentous hemagglutinin outer membrane protein and 1 each for a YadA domain-containing protein (Table 20).

TABLE 17

Number of indels present in isolates from group 1 analysis of virulence-associated genes involved in lipooligosaccharide (LOS) biosynthesis or modification.

| | | # of Non-synonymous Indels Present | | | | |
|---|---|---|---|---|---|---|
| Gene Number | Total bp | HS91 | TK #21 | TK #4 | 153-3 | 129PT |
| HSM_0052 | 234 | 1 | 1 | 1 | 1 | * |
| HSM_0164 | 1569 | 0 | 0 | 0 | 0 | * |
| HSM_0204 | 1383 | 0 | 0 | 0 | 0 | 0 |
| HSM_0397 | 930 | 0 | 0 | 0 | 0 | 0 |
| HSM_0572 | 555 | 0 | 0 | 0 | 0 | 0 |
| HSM_0840 | 588 | 0 | 0 | 0 | 0 | 0 |
| HSM_0925 | 1431 | 0 | 0 | 0 | 0 | 0 |
| HSM_0938 | 1167 | 0 | 0 | 0 | 0 | 0 |
| HSM_0975 | 696 | 0 | 0 | 0 | 0 | * |
| HSM_0977 | 834 | 0 | 1 | 0 | * | * |
| HSM_0978 | 816 | 0 | 0 | 0 | 0 | * |
| HSM_1062 | 1365 | 0 | 0 | 0 | 0 | 0 |
| HSM_1063 | 888 | 0 | 0 | 0 | 0 | 0 |
| HSM_1117 | 672 | 0 | 0 | 0 | 0 | 1 |
| HSM_1118 | 1020 | 0 | 0 | 0 | 0 | 0 |
| HSM_1256 | 1017 | 0 | 0 | 0 | 0 | 0 |
| HSM_1426 | 903 | 0 | * | * | 0 | * |
| HSM_1667 | 129 | 0 | 0 | 0 | 0 | * |
| HSM_1669 | 876 | 0 | 0 | 0 | * | 0 |
| HSM_1714 | 630 | 0 | 0 | * | 0 | * |
| HSM_1794 | 936 | 0 | 0 | 0 | 0 | * |
| HSM_1832 | 1656 | 0 | 1 | 1 | 1 | 1 |

* Indicates when a gene was found to be missing for that particular isolate.

TABLE 18

Number of indels present in isolates from group 2 analysis of virulence-associated genes involved in lipooligosaccharide (LOS) biosynthesis or modification.

| | | # of Non-synonymous Indels Present | | | | | |
|---|---|---|---|---|---|---|---|
| Gene Number | Total bp | TK | HS91 | TK | 2336 | TK | HS91 | 129PT |
| HSM_0052 | 234 | 1 | 1 | 1 | 1 | 1 | 1 | * |
| HSM_0164 | 1569 | 0 | 0 | 1 | 0 | 1 | 0 | * |
| HSM_0204 | 1383 | 0 | 0 | 0 | 0 | 0 | 0 | 0 |
| HSM_0397 | 930 | 0 | 0 | 0 | 0 | 0 | 0 | 0 |
| HSM_0572 | 555 | 0 | 0 | 0 | 0 | 0 | 0 | 0 |
| HSM_0840 | 588 | 0 | 0 | 0 | 0 | 0 | 0 | 0 |
| HSM_0925 | 1431 | 0 | 0 | 0 | 0 | 0 | 0 | 0 |
| HSM_0938 | 1167 | * | 0 | 0 | 0 | 0 | 0 | 0 |
| HSM_0975 | 696 | 0 | 0 | * | 0 | * | 0 | * |
| HSM_0977 | 834 | 2 | 0 | 0 | 0 | 0 | 0 | * |
| HSM_0978 | 816 | 0 | 0 | 1 | 0 | 1 | 0 | * |
| HSM_1062 | 1365 | 0 | 0 | 0 | 0 | 0 | 0 | 0 |
| HSM_1063 | 888 | 0 | 0 | 0 | 0 | 0 | 0 | 0 |
| HSM_1117 | 672 | 0 | 0 | 0 | 0 | 0 | 0 | 1 |
| HSM_1118 | 1020 | 0 | 0 | 0 | 0 | 0 | 0 | 0 |
| HSM_1256 | 1017 | 0 | 0 | 0 | 0 | 0 | 0 | 0 |
| HSM_1426 | 903 | 0 | 0 | 0 | 0 | 0 | 0 | * |
| HSM_1667 | 129 | * | 0 | 0 | 0 | 0 | 0 | * |
| HSM_1669 | 876 | 0 | 0 | 0 | 0 | 0 | 0 | 0 |
| HSM_1714 | 630 | 0 | * | * | 0 | * | * | * |
| HSM_1794 | 936 | 0 | 0 | 0 | 0 | 0 | 0 | * |
| HSM_1832 | 1656 | 1 | 0 | 1 | 0 | 1 | 0 | 1 |

* Indicates when a gene was found to be missing for that particular isolate.

TABLE 19 (5)

Number of indels present in isolates from group 1 analysis of virulence-associated genes involved in adhesion, colonization, or biofilm formation.

| Gene Number | Total bp | # of Non-synonymous Indels Present | | | | |
|---|---|---|---|---|---|---|
| | | HS91 | TK #21 | TK #4 | 153-3 | 129PT |
| HSM_0077 | 12192 | 0 | 3 | 2 | * | * |
| HSM_0268 | 7119 | 0 | 1 | 1 | * | * |
| HSM_0270 | 3480 | 0 | * | * | * | * |
| HSM_0274 | 1569 | 0 | 1 | 0 | * | * |
| HSM_0338 | 7260 | 0 | * | * | * | * |
| HSM_0346 | 4653 | 0 | 3 | 3 | * | * |
| HSM_0377 | 9948 | 0 | * | * | * | * |
| HSM_0394 | 9870 | 0 | 1 | 1 | * | * |
| HSM_0695 | 924 | 0 | 0 | 0 | 0 | * |
| HSM_0708 | 11025 | 0 | * | * | * | * |
| HSM_0844 | 9417 | 0 | 6 | 6 | 1 | * |
| HSM_0953 | 1227 | 0 | * | * | 1 | 1 |
| HSM_1022 | 11250 | 0 | 4 | 4 | 1 | 6 |
| HSM_1090 | 5268 | 0 | 3 | 3 | 3 | * |
| HSM_1212 | 1170 | 0 | 0 | 0 | 0 | * |
| HSM_1257 | 13971 | 0 | * | * | * | * |
| HSM_1484 | 6540 | 0 | 3 | 4 | * | * |
| HSM_1542 | 7158 | 0 | 6 | 8 | * | * |
| HSM_1571 | 11772 | 0 | * | 4 | 4 | * |
| HSM_1647 | 2124 | 0 | 0 | 0 | 0 | * |
| HSM_1651 | 8235 | 0 | 2 | 1 | 0 | * |
| HSM_1793 | 8277 | 0 | * | * | * | * |
| HSM_1889 | 2193 | 0 | * | * | 0 | * |

* Indicates when a gene was found to be missing for that particular isolate.

TABLE 20 (6)

Number of indels present in isolates from group 2 analysis of virulence-associated genes involved in adhesion, colonization, or biofilm formation.

| Gene Number | Gene Name | Total bp | # of Non-synonymous Indels Present | | | | | | |
|---|---|---|---|---|---|---|---|---|---|
| | | | TK | HS91 | TK | 2336 | TK | HS91 | 129P |
| HSM_007 | YadA | 12192 | 4 | 0 | * | 0 | * | 0 | * |
| HSM_026 | Filament | 7119 | * | 0 | 1 | 0 | 1 | 0 | * |
| HSM_027 | Hemaggl | 3480 | * | 0 | * | 0 | * | 0 | * |
| HSM_027 | Adhesin | 1569 | * | 0 | 0 | 0 | 0 | 0 | * |
| HSM_033 | YadA | 7260 | 3 | 0 | 5 | 0 | 5 | 0 | * |
| HSM_034 | YadA | 4653 | 7 | 0 | 5 | 0 | 5 | 0 | * |
| HSM_037 | YadA | 9948 | 5 | * | 8 | 0 | 8 | * | * |
| HSM_039 | YadA | 9870 | 0 | 1 | 0 | 0 | 0 | 1 | * |
| HSM_069 | Alkaline | 924 | 0 | 0 | 0 | 0 | 0 | 0 | * |
| HSM_070 | YadA | 11025 | * | 0 | * | 0 | * | 0 | * |
| HSM_084 | YadA | 9417 | 1 | 0 | 5 | 0 | 5 | 0 | * |
| HSM_095 | Hemaggl | 1227 | 1 | 0 | 0 | 0 | 0 | 0 | 1 |
| HSM_102 | YadA | 11250 | * | 0 | 7 | 0 | 7 | 0 | 7 |
| HSM_109 | Filament | 5268 | 2 | 3 | 3 | 0 | 3 | 2 | * |
| HSM_121 | Hemaggl | 1170 | * | 0 | 1 | 0 | 1 | 0 | * |
| HSM_125 | YadA | 13971 | * | 0 | * | 0 | * | 0 | * |
| HSM_148 | YadA | 6540 | 4 | 0 | 1 | 0 | 1 | 0 | * |
| HSM_154 | YadA | 7158 | * | 0 | * | 0 | * | 0 | * |
| HSM_157 | YadA | 11772 | * | 0 | * | 0 | * | 0 | * |
| HSM_164 | FhaB | 2124 | 0 | 0 | 0 | 0 | 0 | 0 | * |
| HSM_165 | Filament | 8235 | 0 | 0 | 0 | 0 | 0 | 0 | * |
| HSM_179 | YadA | 8277 | * | * | * | * | * | 0 | * |
| HSM_188 | Peptidase | 2193 | * | * | 0 | 0 | 0 | * | * |

* Indicates when a gene was found to be missing for that particular isolate.

TABLE 21

Number of indels present in isolates from group 1 analysis of virulence-associated genes involved in host invasion or metal uptake.

| Gene Number | Total bp | # of Non-synonymous Indels Present | | | | |
|---|---|---|---|---|---|---|
| | | HS91 | TK #21 | TK #4 | 153-3 | 129PT |
| HSM_0047 | 2754 | 0 | 0 | 2 | 0 | 1 |
| HSM_0749 | 1989 | 1 | * | * | * | 1 |
| HSM_0750 | 2916 | 0 | 2 | 2 | 2 | 4 |
| HSM_0931 | 1779 | 0 | 0 | 0 | 1 | 0 |
| HSM_1089 | 1353 | 0 | 0 | 0 | 0 | * |
| HSM_1160 | 537 | 0 | 0 | * | 0 | * |
| HSM_1168 | 3111 | 0 | 0 | 0 | 0 | 1 |
| HSM_1176 | 261 | 0 | 1 | 1 | 0 | 2 |
| HSM_1726 | 1548 | 0 | 0 | * | 0 | * |
| HSM_1730 | 1605 | 0 | 0 | 0 | 0 | 0 |
| HSM_1962 | 2607 | 0 | 0 | 0 | 0 | 0 |

* Indicates when a gene was found to be missing for that particular isolate.

TABLE 22

Number of indels present in isolates from group 2 analysis of virulence-associated genes involved in host invasion or metal uptake.

| Gene Number | Total bp | # of Non-synonymous Indels Present | | | | | |
|---|---|---|---|---|---|---|---|
| | | TK | HS91 | TK | 2336 | TK | HS91 | 129P |
| HSM_0047 | 2754 | 2 | 0 | 1 | 0 | 1 | 0 | 1 |
| HSM_0749 | 1989 | * | 0 | 1 | 1 | 1 | 0 | 1 |
| HSM_0750 | 2916 | 2 | 0 | 2 | 0 | 1 | 0 | 3 |
| HSM_0931 | 1779 | 0 | 0 | 0 | 0 | 0 | 0 | 0 |

TABLE 22-continued

Number of indels present in isolates from group 2 analysis of virulence-associated genes involved in host invasion or metal uptake.

| Gene Number | Total bp | # of Non-synonymous Indels Present | | | | | | |
|---|---|---|---|---|---|---|---|---|
| | | TK | HS91 | TK | 2336 | TK | HS91 | 129P |
| HSM_1089 | 1353 | 0 | 0 | 1 | 0 | 1 | 0 | * |
| HSM_1160 | 537 | * | 0 | 0 | 0 | 0 | 0 | * |
| HSM_1168 | 3111 | 0 | 0 | 0 | 0 | 0 | 0 | 1 |
| HSM_1176 | 261 | 2 | 0 | 0 | 0 | 0 | 0 | 2 |
| HSM_1726 | 1548 | 0 | * | * | 0 | * | * | * |
| HSM_1730 | 1605 | 0 | 0 | 0 | 0 | 0 | 0 | 0 |
| HSM_1962 | 2607 | 0 | 0 | 0 | 0 | 0 | 0 | 0 |

* Indicates when a gene was found to be missing for that particular isolate.

TABLE 23

Number of indels present in isolates from group 1 analysis of virulence-associated genes involved in stress response, antibiotic resistance, and drug efflux.

| Gene Number | Total bp | # of Non-synonymous Indels Present | | | | |
|---|---|---|---|---|---|---|
| | | HS91 | TK #21 | TK #4 | 153-3 | 129PT |
| HSM_0598 | 1890 | 0 | * | * | 0 | * |
| HSM_1191 | 573 | 0 | * | * | * | * |
| HSM_1448 | 282 | 0 | 0 | 0 | 0 | * |
| HSM_1616 | 981 | 0 | * | * | 0 | * |
| HSM_1624 | 1029 | 1 | * | * | * | * |
| HSM_1728 | 405 | 0 | * | * | * | * |
| HSM_1734 | 624 | 0 | 0 | * | 0 | * |
| HSM_1736 | 333 | 0 | * | * | * | * |
| HSM_1737 | 450 | 0 | * | * | * | * |
| HSM_1741 | 399 | 0 | * | * | * | * |

* Indicates when a gene was found to be missing for that particular isolate.

TABLE 24

Number of indels present in isolates from group 2 analysis of virulence-associated genes involved in stress response, antibiotic resistance, and drug efflux.

| Gene Number | Total bp | # of Non-synonymous Indels Present | | | | | | |
|---|---|---|---|---|---|---|---|---|
| | | TK | HS91 | TK | 2336 | TK | HS91 | 129PT |
| HSM_0598 | 1890 | * | 0 | 0 | 0 | 0 | 0 | * |
| HSM_1191 | 573 | * | 0 | * | 0 | * | 0 | * |
| HSM_1448 | 282 | 0 | 0 | * | 0 | * | 0 | * |
| HSM_1616 | 981 | 0 | 0 | 0 | 0 | 0 | 0 | * |
| HSM_1624 | 1029 | 2 | 2 | * | 1 | * | 2 | * |
| HSM_1728 | 405 | * | * | * | 0 | * | * | * |
| HSM_1734 | 624 | 0 | * | * | 0 | * | * | * |
| HSM_1736 | 333 | * | * | * | 0 | * | * | * |
| HSM_1737 | 450 | * | * | * | 0 | * | * | * |
| HSM_1741 | 399 | * | * | * | 0 | * | * | * |

* Indicates gene was missing from that particular isolate.

There were many similarities for indels missing among the recent isolates and 129PT for virulence-associated genes involved in host invasion and metal uptake. These genes included TonB-dependent receptor (2 indels for each of TK #4 and TK #34, 1 indel for TK #42, TK #28 and 129PT), TbpB (1 indel each for HS91, TK #42, 2336, TK #28, and 129PT), TbpA (2 indels for TK #21, TK #4, 153-3, TK #34, and TK #42, 3 or 4 indels for 129PT (the two analyses resulted in different indel estimates for this isolate), and 1 indel for TK #28), TbpA2 (1 indel for 153-3), hemolysis activation/secretion protein-like protein (1 indel each for TK #42 and TK #28), TonB-dependent hemoglobin/transferrin/lactoferrin family receptor (1 indel for 129PT), and an outer membrane hemin receptor protein (1 indel for TK #21 and TK #4, 2 indels for TK #34 and 129PT). The only gene among the stress response, antibiotic resistance, and drug efflux genes to have any indels was acyltransferase 3. There was 1 non-synonymous indel in HS91 and 2336, and there were 2 in TK #34, HS91 ΔaroC, and HS91 ΔnanPU.

* * *

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09592283B2). An electronic copy of the "Sequence Listing" will also be available from the USPTO upon request and payment of the fee set forth in 37 CFR 1.19(b)(3).

What is claimed is:

1. A genetically engineered, non-naturally-occurring, attenuated *Histophilus somni* (*H. somni*) strain, wherein the attenuated strain has deletion of the genes HSM_0270, HSM_0338, HSM_0377, HSM_0598, HSM_708, HSM_0749, HSM_0953, HSM_1160, HSM_1191, HSM_1257, HSM_1426, HSM_1616, HSM_1624, HSM_1714, HSM_1726, HSM_1728, HSM_1730, HSM_1734, HSM_1736, HSM_1737, HSM_1741, HSM_1793, and HSM_1889 to eliminate the ability of the genes to express their cognate wild type gene products, relative to a reference virulent *H. somni* strain, and wherein the attenuated strain possesses in its genome the genes HSM_0052, HSM_0077, HSM_0164, HSM_0268, HSM_0274, HSM_0346, HSM_0394, HSM_0695, HSM_0844, HSM_0975, HSM_0977, HSM_0978, HSM_1089, HSM_1090, HSM_1212, HSM_1448, HSM_1484, HSM_1542, HSM_1571, HSM_1647, HSM_1651, HSM_1667, HSM_1669 and HSM_1794 relative to the reference virulent *H. somni* strain.

2. A vaccine composition comprising a pharmaceutically acceptable vehicle, diluent or excipient and an amount of the genetically engineered attenuated *H. somni* strain of claim 1 effective to elicit a protective immune response against a virulent strain of *H. somni* in a bovine animal.

3. The vaccine of claim 2, wherein the vaccine is in the form of a formulation for intranasal or parenteral administration.

4. The vaccine of claim 2, wherein the reference virulent strain comprises a genomic DNA sequence, which encodes and expresses 100% of the same genes as does a strain of *H. somni* having the sequence set forth in SEQ ID NO: 2.

5. The vaccine of claim 2, wherein the attenuated *H. somni* strain encodes and expresses at least 99% of the same genes as does an attenuated *H. somni* strain having in its genome the sequence of SEQ ID NO: 1.

6. The vaccine of claim 2, wherein the attenuated *H. somni* strain encodes and expresses 100% of the same genes as does an attenuated *H. somni* strain having in its genome the sequence of SEQ ID NO: 1.

7. The vaccine of claim 2, wherein the attenuated *H. somni* strain encodes and expresses at least 99% of the same genes as does the attenuated *H. somni* strain deposited under the designation PTA-121029.

8. The vaccine of claim 7, wherein the attenuated *H. somni* strain encodes and expresses 100% of the same genes as does the attenuated *H. somni* strain deposited under the designation PTA-121029.

9. The vaccine of claim 8, wherein the composition is non-adjuvanted.

10. The vaccine of claim 8, wherein the composition further comprises at least one additional antigen capable of eliciting a pathogen-specific immune response in a bovine animal.

11. The vaccine of claim 10, wherein the at least one additional antigen is capable of eliciting the immune response in the bovine animal against bovine respiratory disease complex (BRDC), bovine respiratory syncytial virus (BRSV), bovine viral diarrhea (BVD), bovine parainfluenza 3 (PI3), infectious bovine rhinotracheitis (IBR), bovine herpesvirus-1 (BHV-1), or bluetongue disease virus (BTV).

12. A method of eliciting a protective immune response in a bovine animal in need thereof against a subsequent virulent *H. somni* infection comprising the step of administering to the bovine animal an effective amount of the vaccine of claim 8.

13. The method of claim 12, wherein the administering is by intranasal, subcutaneous, or intramuscular route.

* * * * *